(12) United States Patent  
Baker

(10) Patent No.: US 9,207,194 B2  
(45) Date of Patent: Dec. 8, 2015

(54) PHASE-SENSITIVE TWO-DIMENSIONAL NEUTRON SHEARING INTERFEROMETER AND HARTMANN SENSOR

(71) Applicant: Lawrence Livermore National Security, LLC, Livermore, CA (US)

(72) Inventor: Kevin L. Baker, San Jose, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 309 days.

(21) Appl. No.: 13/789,327

(22) Filed: Mar. 7, 2013

(65) Prior Publication Data

US 2014/0252240 A1  Sep. 11, 2014

(51) Int. Cl.

| | |
|---|---|
| *G01N 23/05* | (2006.01) |
| *G01N 23/00* | (2006.01) |
| *G01N 23/02* | (2006.01) |
| *G01N 23/04* | (2006.01) |
| *G01N 23/06* | (2006.01) |
| *G01N 23/09* | (2006.01) |

(52) U.S. Cl.
CPC ........... *G01N 23/05* (2013.01); *G01N 23/00* (2013.01); *G01N 23/005* (2013.01); *G01N 23/025* (2013.01); *G01N 23/04* (2013.01); *G01N 23/06* (2013.01); *G01N 23/09* (2013.01); *G21K 2201/068* (2013.01); *G21K 2207/005* (2013.01)

(58) Field of Classification Search
CPC ..... G01N 23/00; G01N 23/005; G01N 23/02; G01N 23/025; G01N 23/04; G01N 23/05; G01N 23/06; G01N 23/09
See application file for complete search history.

(56) References Cited

U.S. PATENT DOCUMENTS

| | | | |
|---|---|---|---|
| 6,337,265 B1 * | 1/2002 | Trezza et al. | 438/612 |
| 8,314,400 B2 | 11/2012 | Nikolic et al. | |
| 8,351,569 B2 | 1/2013 | Baker | |
| 8,558,188 B2 | 10/2013 | Nikolic et al. | |
| 2010/0027739 A1 * | 2/2010 | Lanza et al. | 378/37 |
| 2010/0316190 A1 * | 12/2010 | Baker | 378/82 |
| 2012/0043632 A1 * | 2/2012 | Nikolic et al. | 257/429 |

OTHER PUBLICATIONS

Baker, K.L., "Characterization of the DT Ice Layer in a Fusion Capsule Using a Two-Dimensional X-ray Shearing Inteferometer," Proc. SPIE 7801, Advances in Metrology for X-ray and EUV Optics III, 78010F, Sep. 1, 2010. Retrieved from internet [Mar. 6, 2015]; Retrieved from <doi.10.1117/12.859932>.*
Grunzweig et al., "Design, Fabrication, and Characterization of Diffraction Gratings for Neutron Phase Contrast Imaging," Rev. of Scien. Instr., 79, pp. 0537030-1 to 0537030-6 (2008).
Pfeiffer et al., "Neutron Phase Imaging and Tomography," Phys. Rev. Lett., 96, pp. 215505-1 to 215505-1, (2006).
Rauch et al., "Test of a Single Crystal Neutron Interferometer," Phys. Lett., vol. 47A, No. 5, pp. 369-371, (1974).
Strobl et al., "First Realisation of a Three-Dimensional Refraction Contrast Computerised Neutron Tomography," Nucl Instr. and Meth. in Phys. Res., B 222, pp. 653-653, (2004).
Strobl et al., "On Neutron Phase Contrast Imaging," Nucl. Instr. and Meth. in Phys. Res., , B 266, pp. 181-186, (2008).

* cited by examiner

*Primary Examiner* — Yara B Green
(74) *Attorney, Agent, or Firm* — John P. Wooldridge

(57) ABSTRACT

A neutron imaging system detects both the phase shift and absorption of neutrons passing through an object. The neutron imaging system is based on either of two different neutron wavefront sensor techniques: 2-D shearing interferometry and Hartmann wavefront sensing. Both approaches measure an entire two-dimensional neutron complex field, including its amplitude and phase. Each measures the full-field, two-dimensional phase gradients and, concomitantly, the two-dimensional amplitude mapping, requiring only a single measurement.

16 Claims, 18 Drawing Sheets

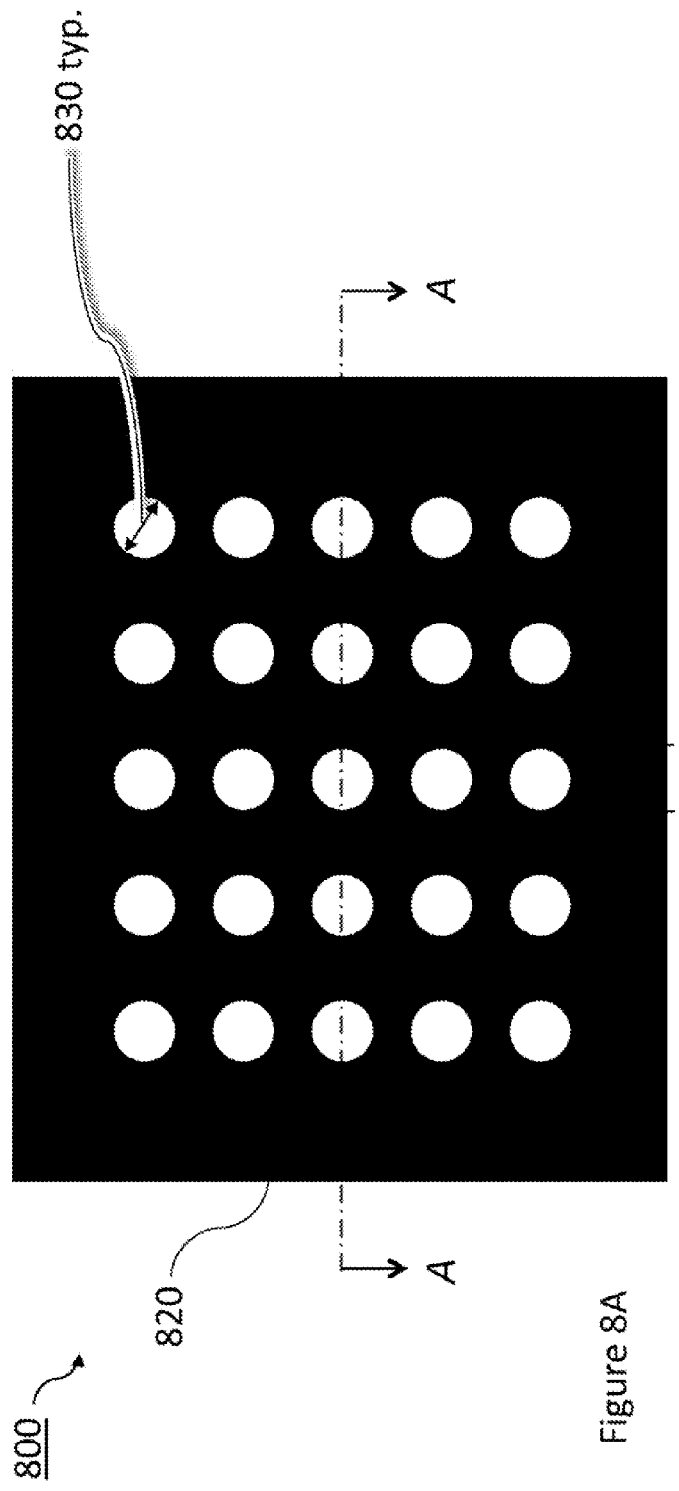
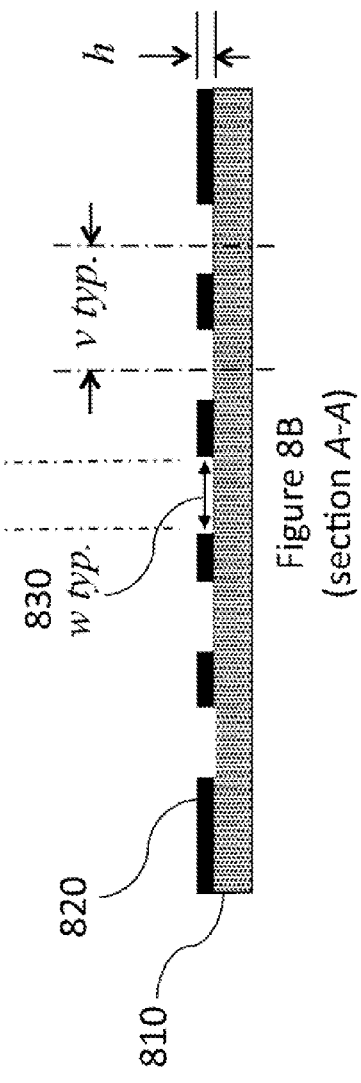
Figure 8A
Figure 8B (section A-A)

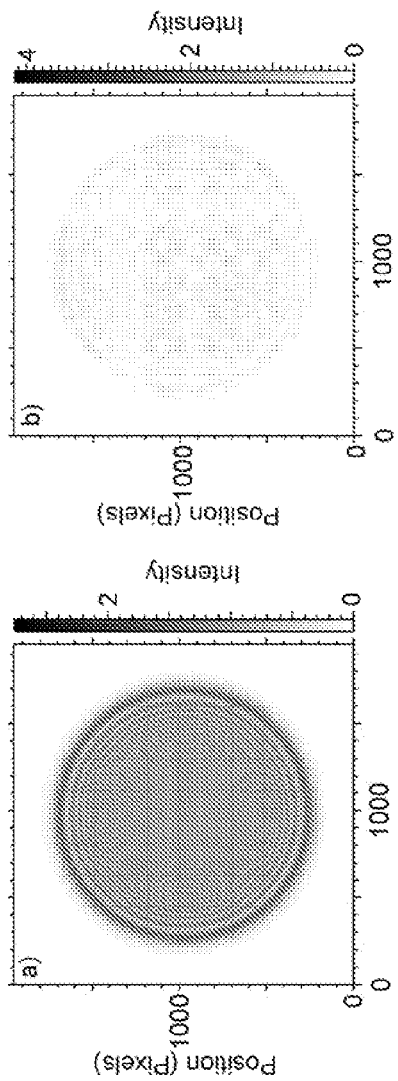
Figure 14A
Figure 14B
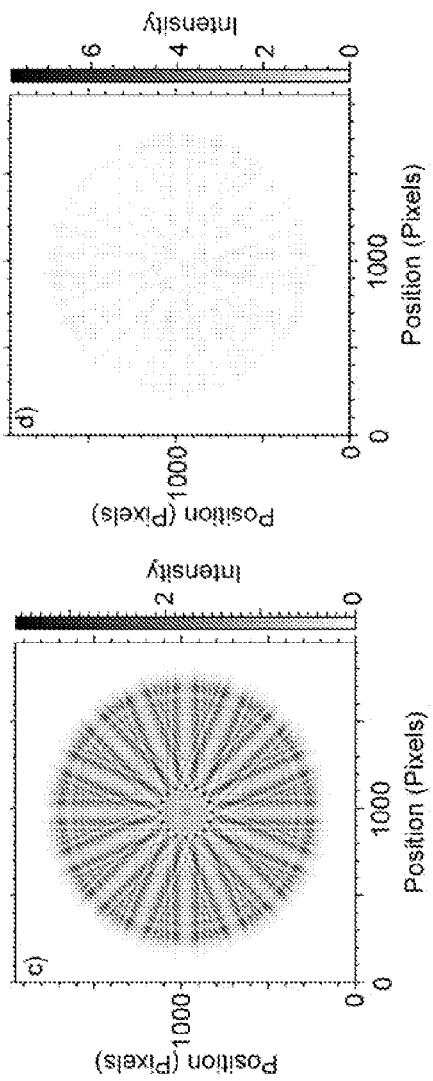
Figure 14C
Figure 14D

PHASE-SENSITIVE TWO-DIMENSIONAL NEUTRON SHEARING INTERFEROMETER AND HARTMANN SENSOR

STATEMENT REGARDING FEDERALLY SPONSORED RESEARCH OR DEVELOPMENT

The United States Government has rights in this invention pursuant to Contract No. DE-AC52-07NA27344 between the U.S. Department of Energy and Lawrence Livermore National Security, LLC, for the operation of Lawrence Livermore National Laboratory.

BACKGROUND OF THE INVENTION

1. Field of the Invention

The present invention relates to neutron imaging, and more specifically, it relates to phase-sensitive neutron imaging and absorption-based neutron imaging.

2. Description of Related Art

Neutron imaging, and, more specifically, phase-sensitive neutron imaging and absorption-based neutron imaging, can provide detailed material as well as spatial information of samples on an atomic level for a variety of applications, ranging from biological imaging to non-destructive testing. This diagnostic complements other radiographic modalities, examples of which include x-ray, THz, e-beam, optical coherence tomography and MRI imaging systems. These systems differ fundamentally owing to the interaction of the specific probe beam with the electronic and/or nuclear properties of a given material. Furthermore, the wavelength of an EM wave or the de Broglie wavelength of a particle provide constraints in terms of the scale size of various features or defects that can be imaged, and moreover, the depth in a given workpiece to which the diagnostic can reveal meaningful information.

The prior art in phase-sensitive neutron imaging techniques includes single crystal interferometry, diffraction-enhanced imaging, phase-contrast imaging and Moiré deflectometry, to achieve higher sensitivity over absorption only measurements. The interferometric class of diagnostics requires high temporal coherence of the incident neutron probe; and, diffraction-enhanced imaging systems require many angular rotations to fully map out the phase distribution. Phase-contrast imaging requires multiple images to detect all of the spatial scales necessary to obtain the desired information. Finally, at present, Moiré deflectometers which have been implemented to date, only measure the gradients in one dimension, and therefore, require multiple measurements in orthogonal directions to obtain the entire two-dimensional field.

In the case of wavefront sensing in the visible (optical) regime, prior art exists, including a two-dimensional shearing interferometer based on crossed phase gratings. As an example, a crossed phase grating in the optical domain was formed by etching a "chessboard" (or, equivalently, a "checkerboard") pattern of alternating optical phase shifts into a glass substrate. Moreover, in the visible regime, prior art exists based upon two-dimensional Hartmann sensors using, as an example, phase screens and lenslet arrays to extract the wavefront of an incident optical beam to the system. However, the implementation of these wavefront-sensing techniques to the domain of neutron wavefront sensing, has not, to Applicant's knowledge, been considered.

A shearing interferometer is a diagnostic tool that enables one to determine the shape of a wavefront, or, equivalently, its spatial phase map, by producing an intensity pattern consistent with the gradient of the equiphase surfaces of the incident beam. The intensity pattern results from the interference of the incident beam, with an angularly displaced replica of itself. Hence, the gradient of the phasefront is effectively transformed into an intensity map. In the case of a plane wave, the resultant intensity pattern consists of a set of parallel fringes. In the case of a converging or diverging beam, the intensity pattern consists of concentric rings, consistent with the curvature of the equiphase surfaces of the incident beam, etc. In the case of making the source spatially coherent, prior art include the use of an aperture or pinhole placed between the neutron source and the object as well as a 1-D periodic amplitude mask.

SUMMARY OF THE INVENTION

An aspect of the invention is an apparatus for two-dimensional neutron imaging, phase and amplitude, of a sample object, including a beam coherence generator, e.g., a 2-D periodic cross Ronchi grating, on which a neutron beam is incident and which transmits a substantially coherent neutron beam therethrough; a two-dimensional structure with periodic features in a pair of transverse orthogonal dimensions spaced from the beam coherence generator, the sample (object) being positioned between the beam coherence generator and the structure so that the coherent beam from the beam coherence generator passes through the sample (object) and the resulting encoded beam is incident on the structure; and a neutron detector positioned after the two-dimensional structure to detect both phase shift and absorption of neutrons passing through the sample (object).

The beam coherence generator is a pinhole or a two-dimensional amplitude Ronchi grating, two 1-D Ronchi gratings rotated 90 degrees to one another. The two-dimensional structure is a crossed phase grating or a two-dimensional Hartmann mask or screen.

BRIEF DESCRIPTION OF THE DRAWINGS

The accompanying drawings, which are incorporated into and form a part of the disclosure, illustrate embodiments of the invention and, together with the description, serve to explain the principles of the invention.

FIG. 8A shows frontal ("beam's eye")-view details of a two-dimensional Hartmann screen of the invention.

FIG. 8B shows cross-sectional details of the two-dimensional Hartmann screen of FIG. 8A along line A-A.

FIG. 14A shows a simulated intensity profile at the entrance of a Hartmann-screen of the wavefront sensor, without a phase object in the beam path.

FIG. 14B shows a simulated intensity profile at 15 mm downstream of, and, after passage through, the Hartmann-screen of the wavefront sensor, without a phase object in the beam path.

FIG. 14C shows a simulated intensity profile at the entrance of a Hartmann-screen of the wavefront sensor, with a test phase object in the beam path.

FIG. 14D shows a simulated intensity profile at 15 mm downstream of, and, after passage through, the Hartmann-screen of the wavefront sensor, with a test phase object in the beam path.

DETAILED DESCRIPTION OF THE INVENTION

Figure 1:
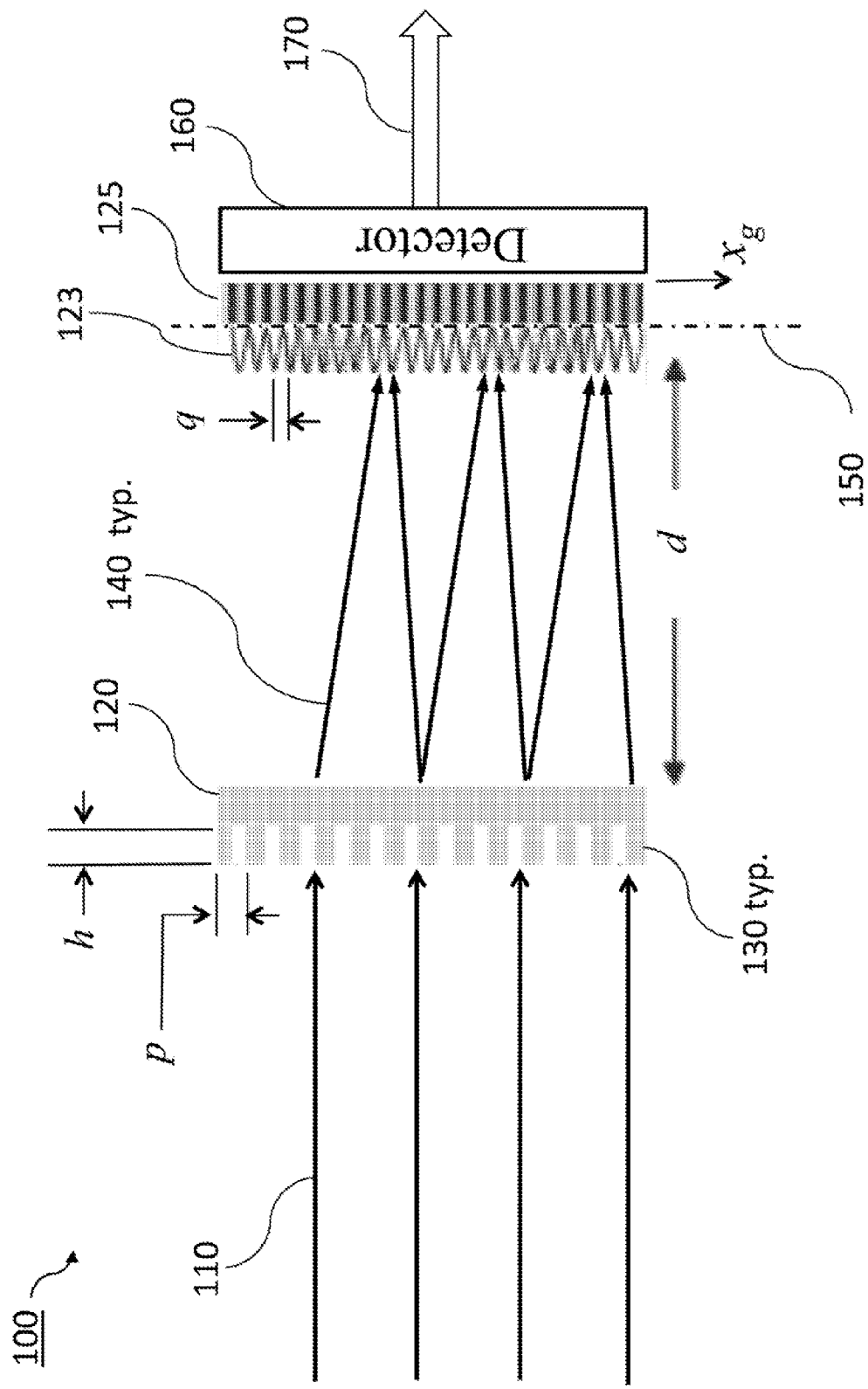
FIG. 1 depicts a prior-art one-dimensional neutron shearing interferometer.

This invention is a robust neutron imaging system that can detect both the phase shift and absorption of neutrons passing through an object. By proper selection of materials, the phase shift term can be four or more orders of magnitude greater than the absorption term, thereby providing a higher sensitivity over current absorption-only measurements.

This invention circumvents many of the prior-art constraints and limitations, resulting in a compact, robust diagnostic with a high level of performance. The two embodiments described herein measure the full-field, two-dimensional phase gradients and, concomitantly, the two-dimensional amplitude mapping, requiring only a single measurement. One of ordinary skill in the art will appreciate that other approaches, based on the teachings that follow, can also be realized and fall within the scope of this invention. As an example, the embodiments described herein can accommodate other classes of particle beam probes, such as electrons and atoms, which could be used to study phase-sensitive and/or absorptive imaging of various samples.

Neutrons are complementary to x rays. Unlike x rays, neutrons interact with cross section that is relatively independent of the atomic number. Neutrons are highly penetrating and are able to non-destructively probe large structures. Neutrons have a mass, $m_n=1.67\times10^{-27}$ kg, which results in a de Broglie wavelength, $\lambda$, in angstroms, as given by $$\lambda = \frac{h}{m_n v} = \frac{39.6}{v}, \quad (1)$$

where $h=6.63\times10^{-34}$ Joule-seconds is Planck's constant and v is the neutron velocity in m/s. The neutron energy, E in units of eV, is given by $$E = \frac{1}{2}m_n v^2 = 5.23\times10^{-9}v^2, \quad (2)$$

Thermal neutrons, neutrons possessing an energy distribution based upon room temperature, 300° K or 0.0259 eV, will have a velocity of 2200 m/s and a wavelength of 1.8 angstroms. Neutrons also have a spin of ½ and a nuclear magnetic moment of $-0.967\times10^{-26}$ J/T enabling them to respond to external magnetic fields and interact with the magnetic moments of unpaired electrons in matter.

The passage of neutrons through a sample can be described by a complex index of refraction, $n=1-\delta-i\beta$, where $\delta$ represents a phase shift and $\beta$ represents absorption. For thermal neutrons, the phase-shift term in certain elements can be up to four or five magnitudes greater than the absorption term. As neutrons pass through the sample, the different elements result in different phase shifts, thereby causing distortion of the wavefront and refraction of the neutrons.

Table 1 shows a tabular summary of selected atomic species, listing their respective neutron phase shift coefficients and absorption coefficients, as well as the ratio of the two, for typical elements that may comprise components of the embodiments discussed herein. Attention is drawn to Silicon (Si) and Gadolinium (Gd). These two elements possess similar phase-shifting properties, yet, their respective neutron absorption coefficients differ by over five orders of magnitude. Hence, as discussed below, Si is a good choice as a low-loss neutron phase shifter, whereas Gd is a good choice as a neutron absorber or beam block of relatively high opacity. More specifically, Table 1 shows relevant parameters for the complex neutron refractive index, $n=1-\delta+i\beta$, of several candidate materials for use as neutron phase shifters and absorption masks, at a nominal wavelength of 4 nm.

TABLE 1

| Material | δ | β | δ/β |
|---|---|---|---|
| Al | $5.3 \times 10^{-6}$ | $9.8 \times 10^{-11}$ | $5.4 \times 10^{4}$ |
| Si | $5.3 \times 10^{-6}$ | $6.0 \times 10^{-11}$ | $8.7 \times 10^{4}$ |
| Ti | $-5.0 \times 10^{-6}$ | $2.4 \times 10^{-9}$ | $-2.0 \times 10^{3}$ |
| Mn | $-7.8 \times 10^{-6}$ | $7.7 \times 10^{-9}$ | $-1.0 \times 10^{3}$ |
| Cu | $1.7 \times 10^{-5}$ | $2.3 \times 10^{-9}$ | $7.3 \times 10^{3}$ |
| Gd | $5.0 \times 10^{-6}$ | $1.1 \times 10^{-5}$ | $4.8 \times 10^{-1}$ |
| Pb | $7.9 \times 10^{-6}$ | $4.0 \times 10^{-11}$ | $2.0 \times 10^{5}$ |

FIG. 1 shows a prior art one-dimensional neutron shearing interferometer 100. An incident neutron beam 110 strikes a one-dimensional phase line-grating 120 consisting of a series of linear, parallel phase-shifting elements, 130, with period, p; width of the grating phase-shifting element, q; and height of the phase-shifting element, h. The phase grating, 120, diffracts several beams, 140, at angles consistent with the Bragg condition, as is known in the art. These Bragg diffracted beams 140 form a neutron interference pattern 123 at plane, 150, located at a distance, d, downstream of the grating 120. In the case of an incident (neutron) plane wave (for beam 110), and a phase grating 120 with a 50% duty cycle (q=p/2), the interference pattern 123 will consist of a set of periodic, parallel intensity fringes at plane 150 with a period of p/2 (=q) in the $x_g$-direction, as shown in FIG. 1. A neutron absorption grating, 125, with a period of p/2, performs the function of an analyzer. As the analyzer grating 125 is translated along the $x_g$-direction, a pattern indicative of the gradient of the neutron wavefront phase is detected by a linear (neutron) detector array, 160. The detector (array) 160 produces a video output signal, 170, which can be integrated along the $x_g$-direction by a post-processor to determine the shape of the incident, one-dimensional neutron wavefront. The basic system, 100, can be considered as a one-dimensional shearing interferometer, as is known in the art.

Figure 2:
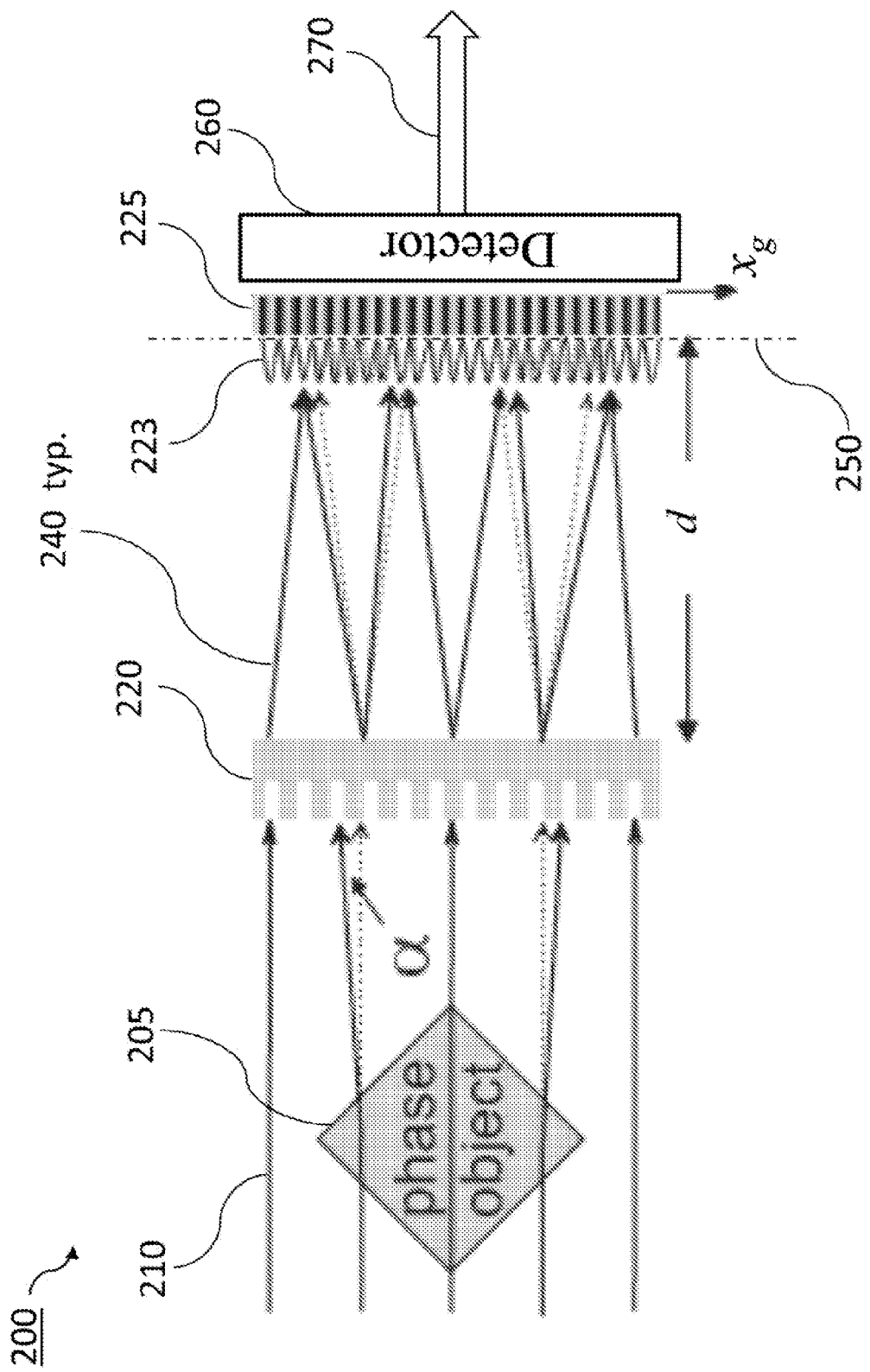
FIG. 2 depicts a prior-art one-dimensional neutron shearing interferometer with a phase object for evaluation.

Turning now to FIG. 2, a prior art one-dimensional shearing interferometer 200 provides one-dimensional spatial phase information of a general phase object 205. The basic interferometer 200 is similar to interferometer 100 shown in FIG. 1. In FIG. 2, however, a phase object, 205, whose phase shifting map is sought, is placed in the path of the incident neutron beam, 210. A composite neutron beam results, consisting of two basic components in this simple example: (1) the original plane wave, resulting from no interaction with the object under test; and (2) a neutron beam component that is refracted and/or diffracted by the object 205, through a small angle, α. Thus the composite neutron beam is the refracted/diffracted component along with the (unmodified) initial beam component. The composite beam is directed to a phase grating, 220, with design parameters similar to those as the phase grating 110 in FIG. 1 (i.e., a grating period, p; the height of the grating lines, h; grating line width, q). The phase grating 220 generates a set of diffracted beams, 240, as before, but, in this case, the diffracted beam is spatially modulated by the presence of the phase object 205, giving rise to several additional refracted and diffracted beam components, 240. These beam components form an interference pattern, 223, with a period of approximately p/2 in the $x_g$-direction, as in FIG. 1, but, now, with additional spatial features, owing to the presence of the phase object 205. A neutron absorption grating, 225, with a period of p/2, and located at plane 250, performs the function of an analyzer. As the grating 225 is translated along the $x_g$-direction, a pattern indicative of the gradient of the neutron wavefront phase, or shear, is detected by a neutron linear detector array, 260. By translating the analyzer (absorption) grating, 225, along the $x_g$-direction, the spatial information obtained by the linear detector (array) 260, provides a video output signal, 270, whose linear, spatial intensity information can be post-processed and integrated along the $x_g$-direction, thereby providing the desired, one-dimensional phase map of the test object, 205.

The embodiments described herein are based on two different neutron wavefront sensor techniques: 2-D shearing interferometry and Hartmann wavefront sensing. Both approaches are capable of measuring an entire two-dimensional neutron complex field, including its amplitude and phase. Moreover, as opposed to the prior art, which requires multiple measurements to characterize a neutron field in a single dimension, the embodiments described herein can characterize a two-dimensional neutron field with only a single measurement. In addition, the sensors described herein obviate the need for an analyzer (e.g., the absorptive grating in the prior art), and, hence, a linear translation capability is not necessary. Finally, these wavefront sensors do not require a temporally coherent source and are compatible with both thermal neutron sources and spallation neutron sources.

As described below, these features stem from three basic, yet, interrelated, aspects of the embodiments: (1) the one-dimensional phase grating of the prior art is replaced with a two-dimensional structure, with periodic features in each transverse direction; (2) the sensor is configured as a Talbot imaging system, as enabled by the periodic nature of the structure; (3) the neutron source employs a single pinhole or a two-dimensional Ronchi grating, the latter to generate multiple neutron beamlets that are pairwise coherent in both transverse directions.

In the case of a two-dimensional shearing interferometer, the structure can be in the form of a two-dimensional crossed phase grating, whereas, in the case of a two-dimensional Hartmann sensor, the structure can be in the form of a two-dimensional array of holes, or subapertures. In either case, the two-dimensional structure can be fabricated onto a single membrane or cut and/or etched from a single thin film, making it insensitive to both vibrations and alignment.

A. Two-Dimensional Neutron Shearing Interferometers

A.1. Basic System Configuration and Grating Embodiments

Figure 3:
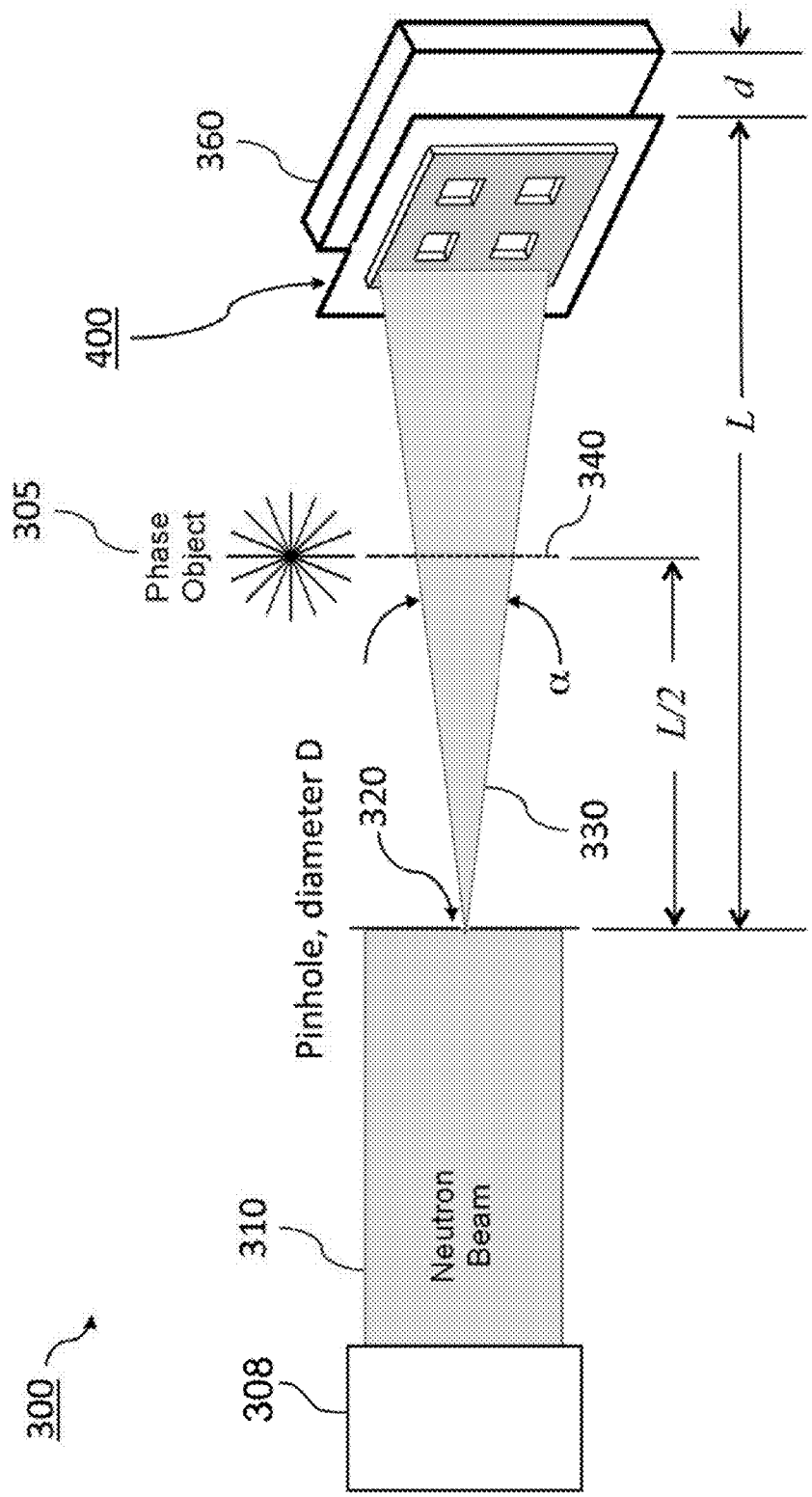
FIG. 3 depicts a two-dimensional neutron interferometer of the invention using a crossed phase grating.

In this embodiment, a two-dimensional neutron shearing interferometer (sensor) is comprised of a two-dimensional grating structure placed downstream of the object to be evaluated. FIG. 3 depicts one example of the basic shearing interferometer (system) 300 to enable two-dimensional imaging of a phase object, 305. The system is comprised of a neutron source 308 providing a neutron beam 310 that passes through a pinhole, 320, with a diameter, D, and produces a diffracted (substantially coherent) beam 330, diverging at an angle α, that subsequently propagates through the phase object 305, located at plane 340, positioned at a distance L/2 downstream of the pinhole aperture. The presence of the phase object modifies the neutron beam equiphase surfaces in a spatial manner.

The goal of the sensor is to quantify the two-dimensional phase map of the object 305, as determined by wavefront measurements of the spatially encoded neutron beam. The neutron beam, after passage through the phase object subsequently impinges upon a two-dimensional phase grating, 400, located at a distance, L/2, downstream from the phase object plane, 340, or, equivalently, the grating 400, is located at a distance, L, downstream from the pinhole aperture 320.

The phase grating 400 produces several replicas of the incident wavefront via angularly displaced, Bragg diffracted orders, whose coherent summation is sensed by a two-dimensional detector array, 360, positioned at a distance, d, downstream from the grating, 400. One skilled in the art will appreciate that variations of the basic two-dimensional grating can also provide similar sheared replicas of the incident neutron beam, including a checkerboard pattern of alternating, phase shifting elements.

As shown in FIG. 3, the diameter, D, of the pinhole 320 is subject to the constraint that the neutron beam, 330, emerging from the pinhole aperture possess an diffractive angle, α, of sufficient magnitude so as to illuminate at least one grating pair along each orthogonal axis at the plane of the crossed phase grating 400 located at a distance, L from the pinhole aperture. That is, the diffractive spread of the diverging neutron beam 330 beyond the aperture 320 must be equal to, or, in excess of, the pitch, p, of the grating structure 400 as labeled in FIG. 4D. The phase object 305 to be imaged and characterized is placed at a nominal distance of L/2 downstream of the pinhole. Equivalently, the phase object is located at the mid-plane 340 between the pinhole and the grating. A key component in this two-dimensional shearing interferometer 300 is a crossed phase grating, 400, which produces an intensity pattern on detector, 360, indicative of the two-dimensional wave-front gradient resulting from the propagation of the neutron beam through the phase object 305 under evaluation.

Figure 4:
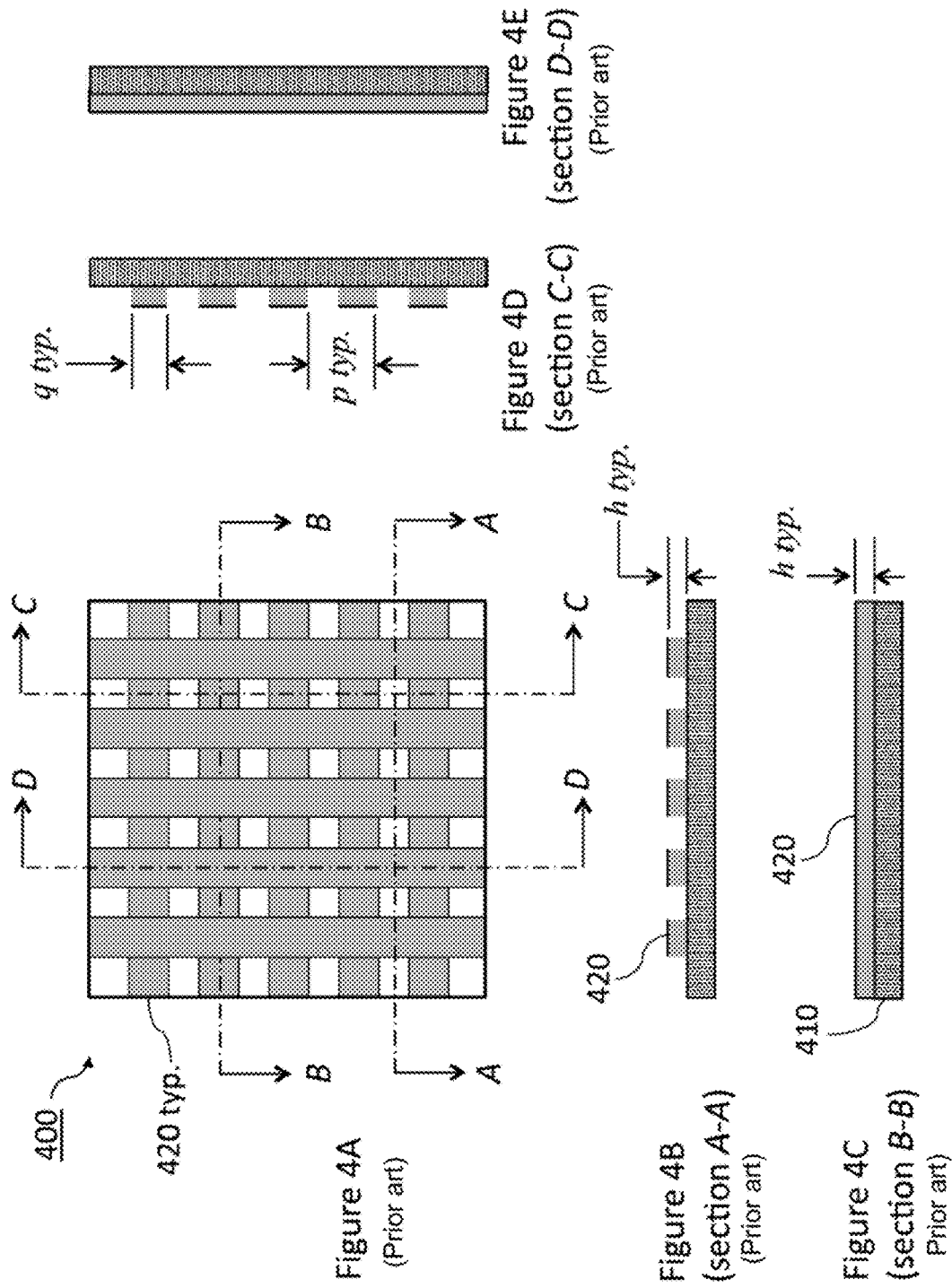
FIG. 4A shows frontal ("beam's eye")-view details of a two-dimensional crossed phase grating of the invention.
FIGS. 4B-E show cross-sectional details of the two-dimensional crossed phase grating of FIG. 4A along lines A-A, B-B, C-C, and D-D respectively.

Details of a typical "crossed" phase grating, 400, are shown in FIGS. 4A-E. FIG. 4A shows a "beam's-eye" (frontal) view of the grating structure, while FIGS. 4B through 4E, inclusive, show relevant cross-sectional views of the same (sections A-A, B-B, C-C and D-D, respectively). Grating 400 is formed of a plurality of spaced parallel grating lines 420 in each orthogonal direction on a substrate 410. As shown in FIGS. 4B and 4D, the pitch of the grating is given by p; and the corresponding width of the grating lines is given by q. As shown in FIGS. 4C and 4E, the height of the grating lines, including the height at the crossed, perpendicular intersections, is the same throughout the plane of the structure and is given by h. In this example, the grating structure is symmetric. That is, each of the two crossed gratings consists of the same grating period and duty cycle. However, this condition (i.e., identical gratings), in general, need not be the case, and is subject to the spatial resolution required along each transverse axis for a given phase object.

The substrate, as well as the grating line structure, is made of a low-loss, transparent material for optimal performance of the neutron imaging interferometer (sensor). An example of a suitable material is Si, whose relevant phase and loss parameters, as tabulated in Table 1, are in the ratio of ≈$10^5$. Hence, owing to the large phase-shift to absorption ratio for Si, the grating structure will be essentially transparent (i.e., lossless) to neutrons, given the thickness of Si required to provide the necessary neutron phase shift of π, which is quantified below. In the case of Si, the overall grating structure, including the substrate, can be fabricated as a rugged, monolithic structure using etching and lithographic techniques known in the art.

A.2. Talbot Imaging

The essential component in the two-dimensional shearing interferometer is a crossed phase grating. The spatial mapping of the image formed on detector 360 is proportional to the gradient of the incident neutron wavefront. Subsequently, by integrating the gradient pattern along each orthogonal transverse axis offline, a two-dimensional phase map of the phase object can be determined.

It is well known in the optics community that, under the proper conditions, an optical field distribution at one plane beyond a periodic structure can be reproduced at another plane, downstream from the first, as first described and demonstrated by Talbot. As is well-known in the art, the Talbot "self-image" is not an image in the most strict sense, for, in the present case, there is not a one-to-one mapping of the incident beam, but, instead, a "redistribution" of the incident field that reforms at various fractional Talbot distances downstream of the grating.

Given the coherent wave nature of a neutron beam, an analogous Talbot effect can be realized for neutrons downstream of a periodic structure, such as a phase grating, through which it propagates. More precisely, if the phase grating is comprised of alternating bars and slits, with respective phase shifts of 0 and π phases, then the field emerging from the grating will form a self-image at a distance, d, equal to $d_T = p^2/2\lambda$ downstream of the phase structure, or grating. (Recall FIG. 3, which indicates the relevant components, the grating 400 the detector 360, and the distance between them, d.) The parameter, $d_T$ is the so-called Talbot distance, p represents the pitch of the phase grating and λ is the wavelength of the source. At a distance, d, equal to $d_T/4$ and $3d_T/4$, the initial phase pattern across the beam has become uniform and the initially uniform intensity has acquired the periodic structure of the initial phase pattern, with the pitch of the intensity pattern equal to one-half the pitch, p, of the original phase grating. Hence, a multi-pixel detector 360 placed at this plane will detect these intensity variations, indicative of the phase map gradient of the object.

Conversely, at a distance, d, downstream of the grating structure, equal to $d_T/2$ along the propagation path, the phase pattern is "reversed" from the original phase grating, resulting in a uniform intensity. Hence, at this particular location along the propagation axis, the system cannot be used for wavefront sensing using direct detection, since there are no transverse intensity features present.

In practice, the intensity pattern has well defined detectable features for propagation distances, d, between $d_T/16$ and $7d_T/16$ and between $9d_T/16$ and $15d_T/16$. Below, simulations of the performance of the crossed-grating shearing interferometer for several phase objects are presented. In these simulations, the distance, d, between the detector 360 and the crossed phase grating was set to a value of d~$d_T/13$. At this distance, the resultant intensity pattern based on the initial phase profile produces a well-defined set of features, indicative of the phase gradient of the neutron beam.

A.3. Design Considerations to Realize a Single Pair of Diffracted Beams from a Phase Grating For optimal shearing interferometer performance, it is desired to constrain the grating structure to produce only two diffracted beams. This follows, since a shearing interferometer requires only one pair of angularly offset, identical copies of a given wavefront, with which to coherently combine, or interfere, so that the gradient phase-map can be realized in the form of an intensity pattern. One can consider the grating as an effective beam splitter, which diffracts a given incident wavefront into a pair of identical wavefront replicas, with a well-defined angular offset between the emerging wavefronts. Given that the shearing interferometer described herein enables a full two-dimensional mapping of a phase object, this grating condition applies to both orthogonal, transverse axes of the crossed phase grating.

One approach to satisfy this requirement is to enhance the diffraction efficiency of one set of diffractive orders (e.g., the m=±1 order), while minimizing all other odd orders and, moreover, suppressing all the even diffractive orders, including the m=0 order. One skilled in the art will appreciate that this requirement can be satisfied in general, so that, as long as one pair of diffracted beams (not necessarily the same diffracted order for each beam) is generated by the grating structure, an optimal shearing function can be realized.

Returning to FIGS. 4A through 4E, each of the two orthogonal (crossed) gratings is designed such that the even Bragg diffraction orders of each respective grating are suppressed, or eliminated. In order for the efficiency of the even orders (not necessarily including the m=0 order) of a transmission grating to go to zero, the width of the grating lines, q, must be one-half that of the grating pitch, p, as is known in the art (i.e., a 50% duty cycle for the grating pattern). This condition leads to the requirement that q=p/2, for each of the respective crossed gratings. In addition, for the efficiency of the m=0 order of the grating to approach zero, the bar structure of each grating line must produce a phase shift of $\pi$ radians relative to the effective slits of the grating. That is, the differential neutron phase shift of the beam component that propagates through a given phase bar and the substrate, relative to that which only propagates through the substrate (the effective "slits"), must be equal to $\pi$ radians.

A.4. Numerical Example of a Crossed-Phase Grating

The passage of neutrons through a sample can be described by a complex index of refraction, expressed as $n=(1-\delta)+i\beta$, where $1-\delta$ gives rise to a phase shift as the neutrons pass through the sample and the $\beta$ term results in absorption. Note that $\delta$ is proportional to $Nb_c(\lambda^2/2\pi)$ where N is the atomic number density, $b_c$ is the average coherent scattering length and $\lambda$ is the de Broglie wavelength. Also, $\beta$ is proportional to $N\sigma\lambda/(4\pi)$, where $\sigma$ is the attenuation cross-section. Using typical values for Silicon, $\lambda$~1.5 nm, N~$5\times10^{28}$ m$^{-3}$ and $b_c$~4.15 fm, one obtains values of $\delta$ of $7.5\times10^{-5}$. The length for a $\pi$ phase shift, $x_\pi$, can be expressed as $x_\pi=\lambda/(2\delta)$ and the absorption length, $x_\mu$, can be written as $x_\mu=\lambda/(4\pi\beta)$.

As previously described, Table 1 shows that Si is a good choice as a low-loss neutron phase shifter, whereas Gd is a good choice as a neutron absorber or a thin-film pinhole mask, the latter of relatively high background opacity. Hence, Si can be used for the crossed-phase grating structure, which can consist of etched or deposited Si thin films onto various substrates, including Si, $Al_2O_3$, etc. This structure is discussed herein as an example for a 2D shearing interferometer.

By contrast, a thin film of Gd, say, grown on a Si substrate, can be used as a mask for a pinhole aperture or for an array of pinholes, as formed lithographically by etching small openings, or holes, into a planar Gd mask. This structure will be discussed below as a mask for a 2D Hartmann wavefront sensor, as well as for a pinhole array to generate pairwise coherent neutron beams.

Returning to FIGS. 4A-E, Si can be used for the crossed-phase grating structure. As is known in the art, a necessary condition for all even diffractive orders, above the $0^{th}$ order (e.g., m=±2, ±4, ±6, . . . ), to go to zero is that the duty cycle of the grating should be 50%; that is, the width of the grating bars, q, should be equal to the width of the effective slits, p−q. Hence, referring to FIG. 4B, D, the width of the bar structure of the grating, q (=p/2), is identical to the width of the slits, p−q=p/2 such that all even orders above m=0 (e.g., m=±2, ±4, ±6, . . . ) go to zero.

Recall, that to suppress the m=0 diffractive order of the grating, the differential phase shift experienced for a given neutron energy, must result in a phase shift of $\pi$. Assuming a source of cold neutrons, the nominal de Broglie wavelength, $\lambda$, is ≈1.5 nm. Given this value for $\lambda$, and, assuming a thin film of Si as the phase shifting element (with the relevant material parameters given in Table 1), the required thickness of the Si, h, is equal to 10.1 μm to provide the necessary phase shift of $\pi$. Referring to FIGS. 4A-E, one can fabricate the crossed phase grating using a Si wafer as the substrate 410, with a crossed grid pattern of Si bars 420, all of thickness, h, of 10.1 μm. For these parameters, the absorption experienced by cold neutrons as they propagate through, and, are diffracted by, the grating is negligible. Thin-film and photolithographic techniques, as are known in the art, can be used to fabricate the crossed grating.

At the design neutron wavelength of 1.5 nm, the efficiency of the m=0 order approaches zero and the efficiency of the m=±1 order is approximately 40%. Finally, as is known in the art, the efficiency of the odd orders scales approximately as $1/m^2$ for the higher-order diffracted beams. Hence, as an example, the amplitude of the next two higher-order beams, the m=±3 and ±5 beams, will be, respectively, ≈1/9 and ≈1/25 that of the first-order diffracted beam. Therefore, any adverse effect of these higher-odd-order beams on the measurements will be negligible.

B. Transverse Coherence Requirements

B.1. Single-Pinhole Neutron Source

Figure 5:
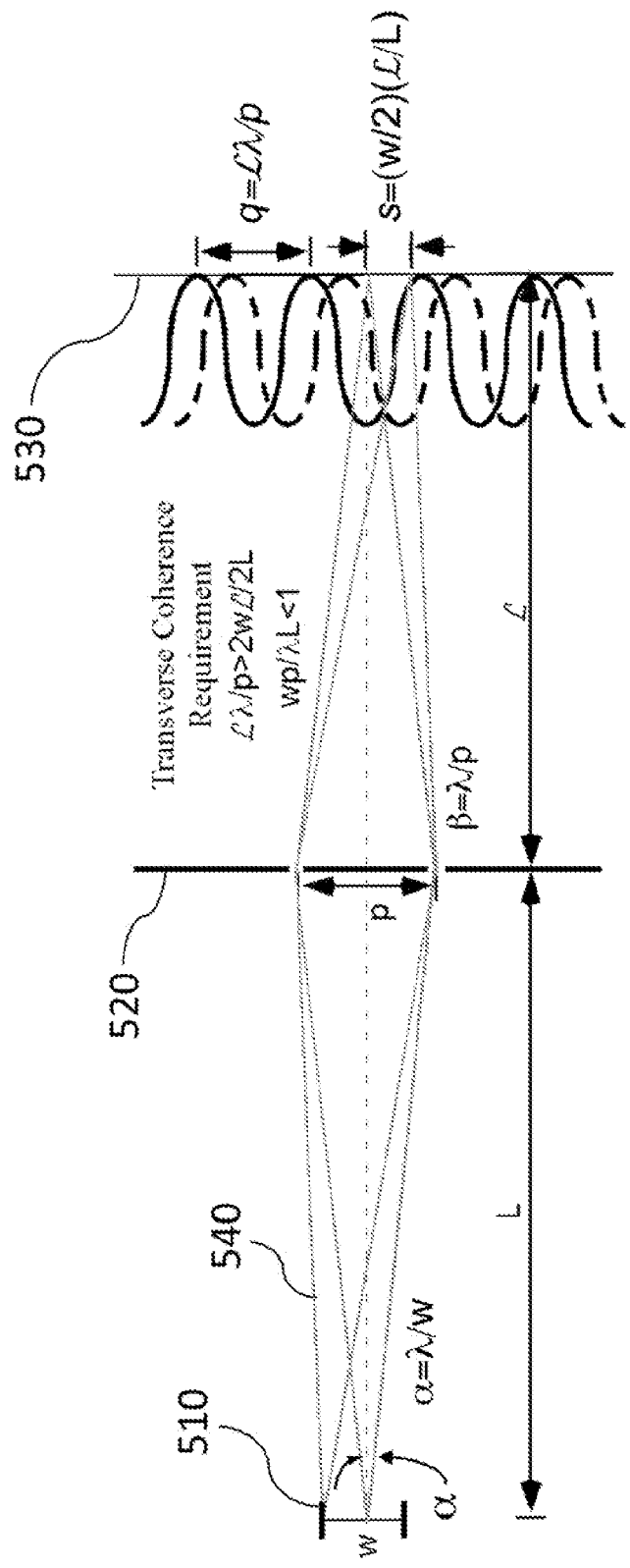
FIG. 5 shows relevant parameters regarding transverse coherency.

The coherency requirements for the two-dimensional neutron shearing interferometer are such that the source is required to be nearly spatially coherent in both transverse directions. This is consistent with using a spatially filtered neutron source. These relevant parameters, for a one-dimensional system (without loss of generality), are displayed in FIG. 5, where the neutron source is represented by a pinhole 510 of diameter w (w corresponds to the diameter, D, of pinhole 320 in FIG. 3). A double slit 520 is used to emulate the relevant parameters of the grating, with a pitch, p (grating 400 in FIG. 3). The double slit "grating" 520 is located at a distance L downstream from the source 510, and, the detector plane 530 is positioned at a distance $\mathcal{L}$ (d in FIG. 3) downstream from the double slit 520.

The key requirement that enables the source to be nearly spatially coherent is that the diameter, w, of pinhole 510 in front of the neutron source be sufficiently small such that the diffractive spreading, $\alpha=\lambda/w$, of the neutron beam 540 at the grating plane 520, exceed the pitch, p, of the grating, or $L\lambda/w>p$, where L is the distance between the source and the grating, $\lambda$ is the wavelength, w is the diameter of the neutron source and p is the pitch of the grating along each transverse axis. The diffraction angle of the beam that emerges from the double slit 520 is given by $\beta=\lambda/p$ (assuming that the "slit apertures" of the grating 520 are sufficiently small so that the overall diffractive envelope is greater than any scale length). It follows that the diffractive spread of the beam at the detector plane 530, located at a distance $\mathcal{L}$ downstream of the slit (grating) is given as $q=\mathcal{L}\beta=\mathcal{L}(\lambda/p)$. Each beamlet that emerges from its respective grating will interfere with the other beamlet, resulting in an interference pattern with a period, q. The lateral distance, or shear, s, between the two interference patterns, can be shown to be equal to be $s=(w/2)(\mathcal{L}/L)$. Note that, under these assumptions, the shear is approximately wavelength independent (i.e., independent of the neutron energy). Note further that, for a symmetrical configuration, $\mathcal{L}/L=1$, the shear is equal to one-half the pinhole aperture (s=w/2). Finally, note that the lateral displacement of the resultant pattern at the detector plane scales as $\mathcal{L}/L$, so, as the plane of the detector 530 is positioned further from the grating 520, the pattern is effectively magnified by this factor.

B.2. Extended Neutron Sources

Extended neutron sources can also be used when the source is appropriately made periodic. A Ronchi grating is an example of one such class of periodic structure. By imposing a periodic pattern onto an extended source, an ensemble of pairwise, interlaced nearly coherent beamlets can be realized. In essence, one can view this as an extension of the double slit structure of FIG. 5 in the lateral direction. By placing two crossed Ronchi rulings or gratings in front of the extended source it can be made to appear as a spatially coherent source as neutrons from the different regions of the source can be made to align the peaks of the diffraction pattern in the same location on the detector, thereby forming good contrast fringes.

Figure 6:
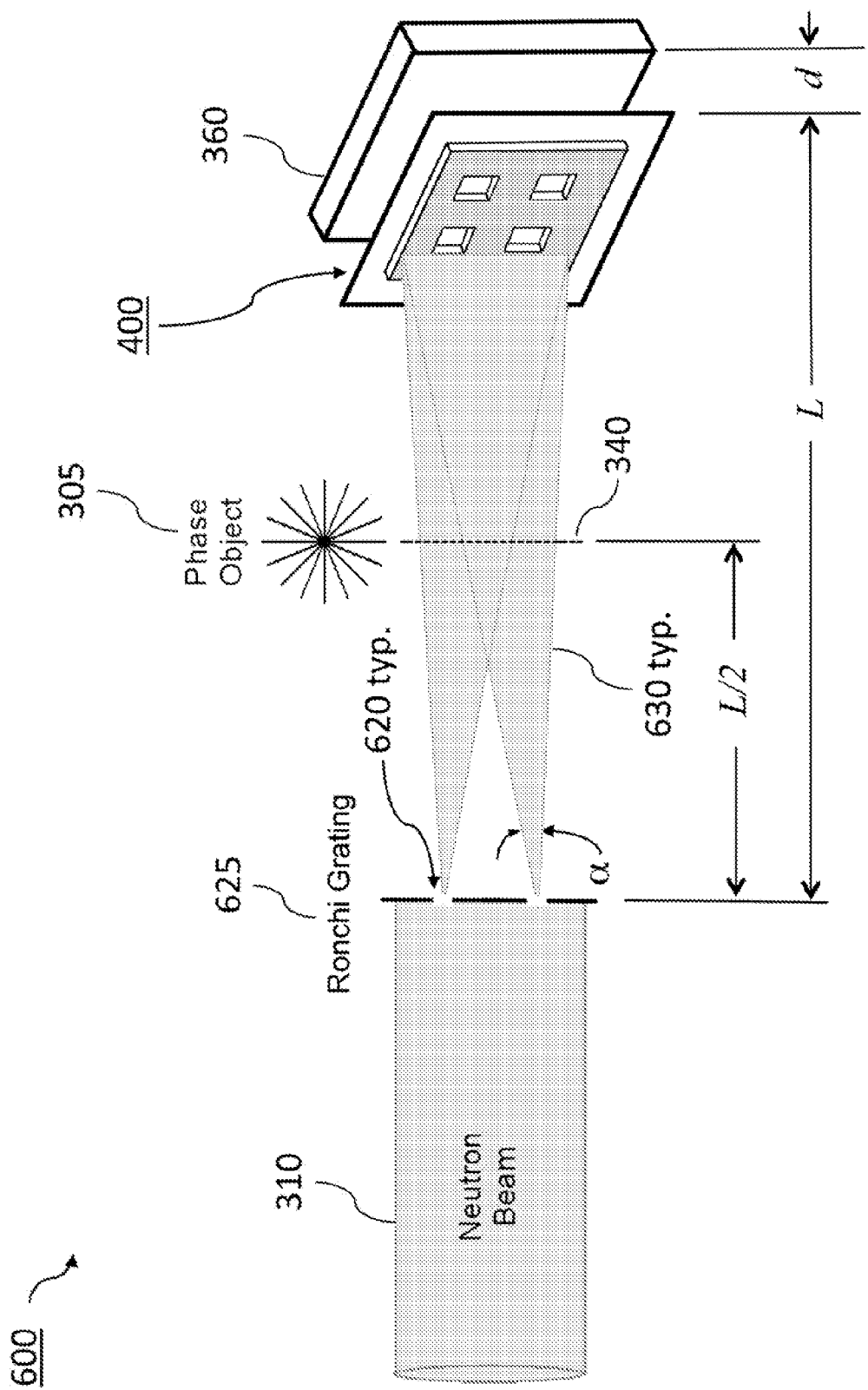
FIG. 6 depicts a two-dimensional neutron interferometer of the invention using a crossed phase grating and a Ronchi extended-source coherency grating.

FIG. 6A shows an example of an embodiment for a shearing interferometer 600, using an extended source (neutron beam) 310, augmented with Ronchi gratings 625. Other than the crossed Ronchi gratings, all the other elements of this embodiment are similar to that of the single-pinhole shearing interferometer shown in FIG. 3. In the present embodiment crossed Ronchi gratings 625 with one pair of pinholes 620 is shown. As is the case of the single pinhole shearing interferometer, the diameter of each pinhole 620 in the present case is chosen such that each respective diffracted beam, 630, will diffract by an angle, α, of sufficient magnitude so that the respective diffractive spread at the crossed grating 400, located at a distance L from the Ronchi gratings will be equal to, or exceed, the grating period, p.

For the case of a two-dimensional shearing interferometer one would utilize a pair of crossed Ronchi rulings at the source. The Ronchi grating has two orthogonal pairs of pinholes. This has the advantage of greatly increasing the amount of neutrons impinging on the sample. The tradeoff here is that a pair of crossed Ronchi gratings will require convolving the measurement with the nearest neighbors, which will affect the high spatial frequency information. The extent of this convolution will then depend upon the original extent of the source relative to the pitch of the crossed Ronchi rulings used to make the original spatially incoherent source into a periodic spatially coherent source. The Ronchi gratings can be fabricated as either amplitude gratings or phase gratings. The phase grating has the advantage of imposing phase shifts onto the incident beam, with little or no appreciable loss.

C. Two-Dimensional Hartmann Sensor

C.1. Basic Neutron Hartmann Wavefront Sensor

The basic Hartmann sensor of the invention is comprised of a mask consisting of an array of subapertures. One such example involves an amplitude mask, whereby the mask is in the form of a highly absorbing structure, with a two-dimensional array of highly transmitting subapertures. The period and duty cycle of the subapertures are designed to be consistent with the required system sensitivity and wavefront resolution. A two-dimensional detector measures the lateral position and intensity level of the resultant neutron pattern. The Hartmann mask, or screen, would therefore consist of a regular array of effective holes, with the lateral displacement of the neutrons traveling through the holes providing phase-gradient information, and, in addition, the amplitude of the neutron pattern providing absorption information.

A key advantage of the Hartmann sensor with respect to interferometric wavefront sensors is that the former class of sensor does not require as stringent requirements placed on the transverse spatial coherence of the source whose wavefront measurement is sought. A basic tradeoff is that the Hartmann sensor is not as sensitive in the case of a low fluence neutron source, and the wavefront resolution is not as great, as its interferometric counterparts.

Figure 7A:
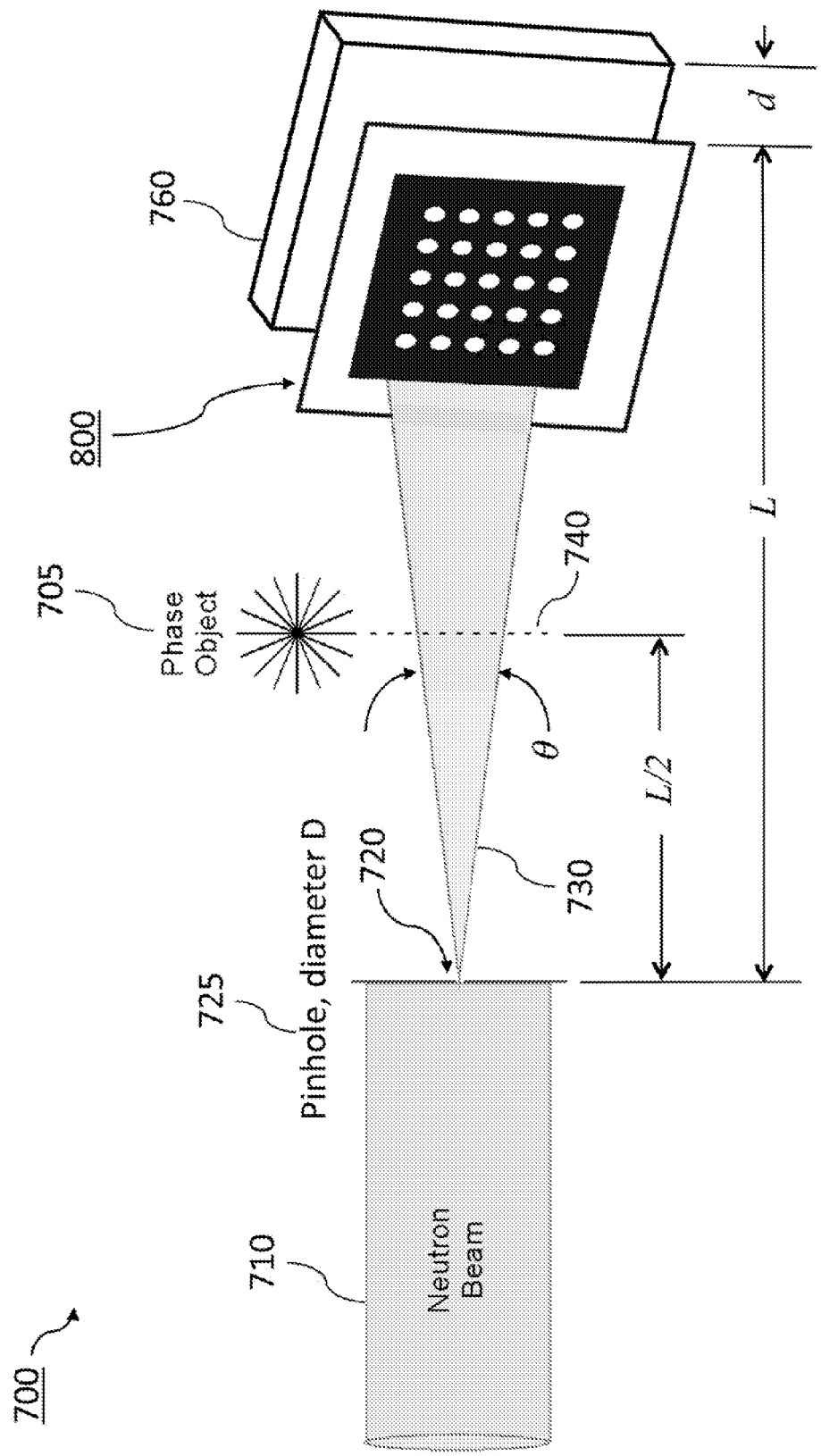
FIG. 7A depicts a two-dimensional neutron of the invention using a Hartmann screen.

FIG. 7A shows an embodiment of a two-dimensional neutron Hartmann sensor 700. The basic system configuration is similar to that of the two-dimensional shearing interferometer (FIG. 3), a key difference being an absorbing mask 800 consisting of an array of lossless apertures, which is used in place of the phase grating 400. The mask is positioned at a distance of L from a neutron source (beam) 710 constrained by an aperture 725, formed with a pinhole 720 of diameter D. The neutron beam 730 emerges from the pinhole 720 with an angular spread, θ, and is directed to illuminate the mask 800. A phase object 705 to be characterized is placed between the neutron source and the Hartmann screen, typically at the mid-plane 740, located at a distance of L/2 from the neutron source. A two-dimensional neutron detector 760 is placed at a distance d downstream of the Hartmann mask 800 with its output containing information as to the local neutron wavefront gradients across the plane.

Figure 7B:
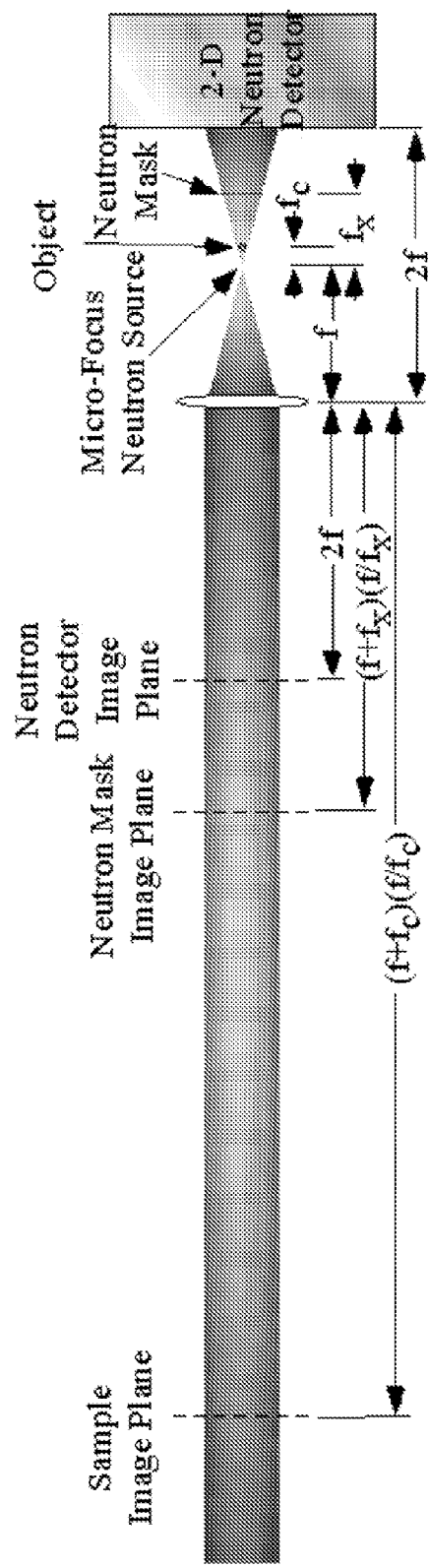
FIG. 7B illustrates curvature wavefront sensor geometry.
Figure 7D:
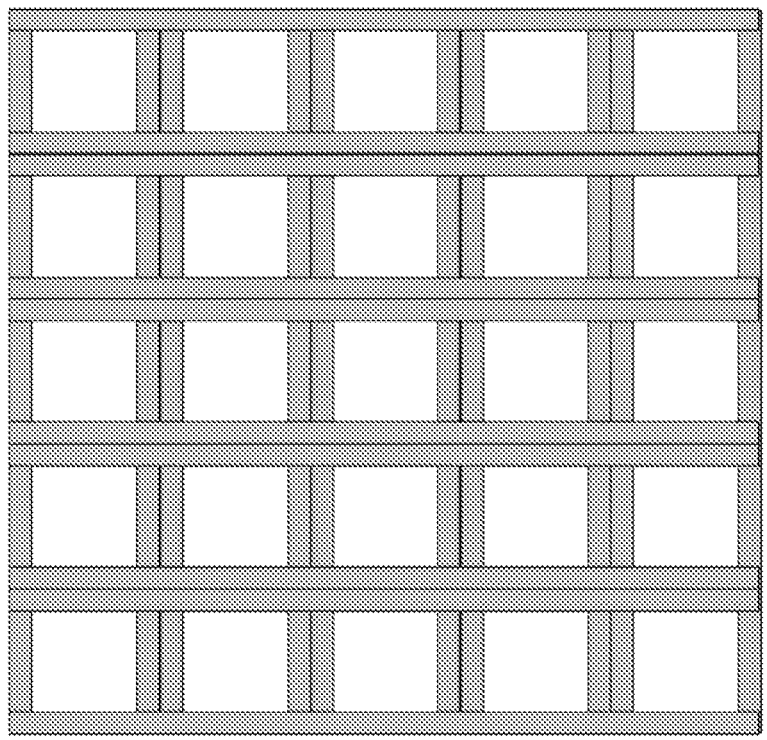
FIG. 7D illustrates an examplary geometry of a Hartmann sensor having an array of neutron zone plates.
Figure 7C:
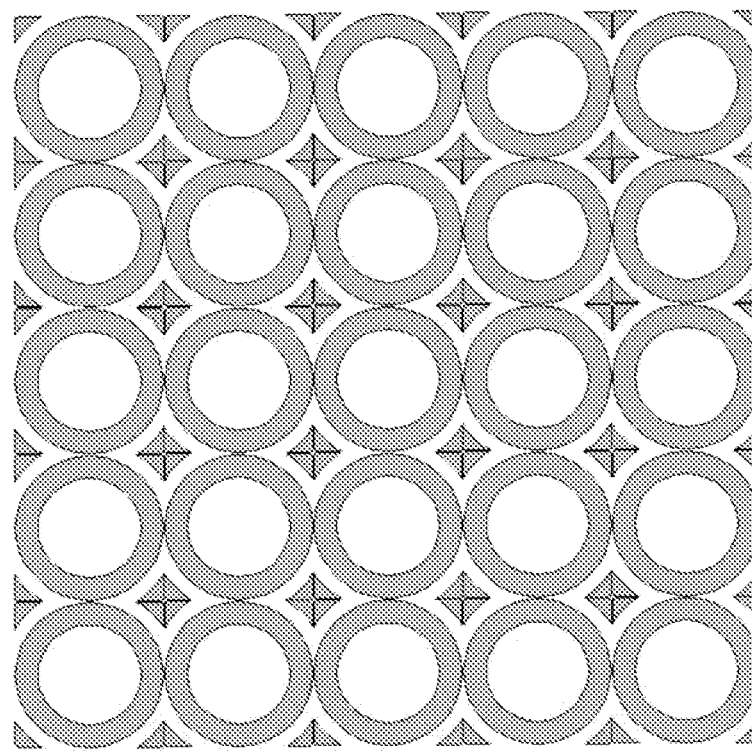
FIG. 7C illustrates an example geometry of a Hartmann sensor having an array of neutron zone plates.
Figure 7E:
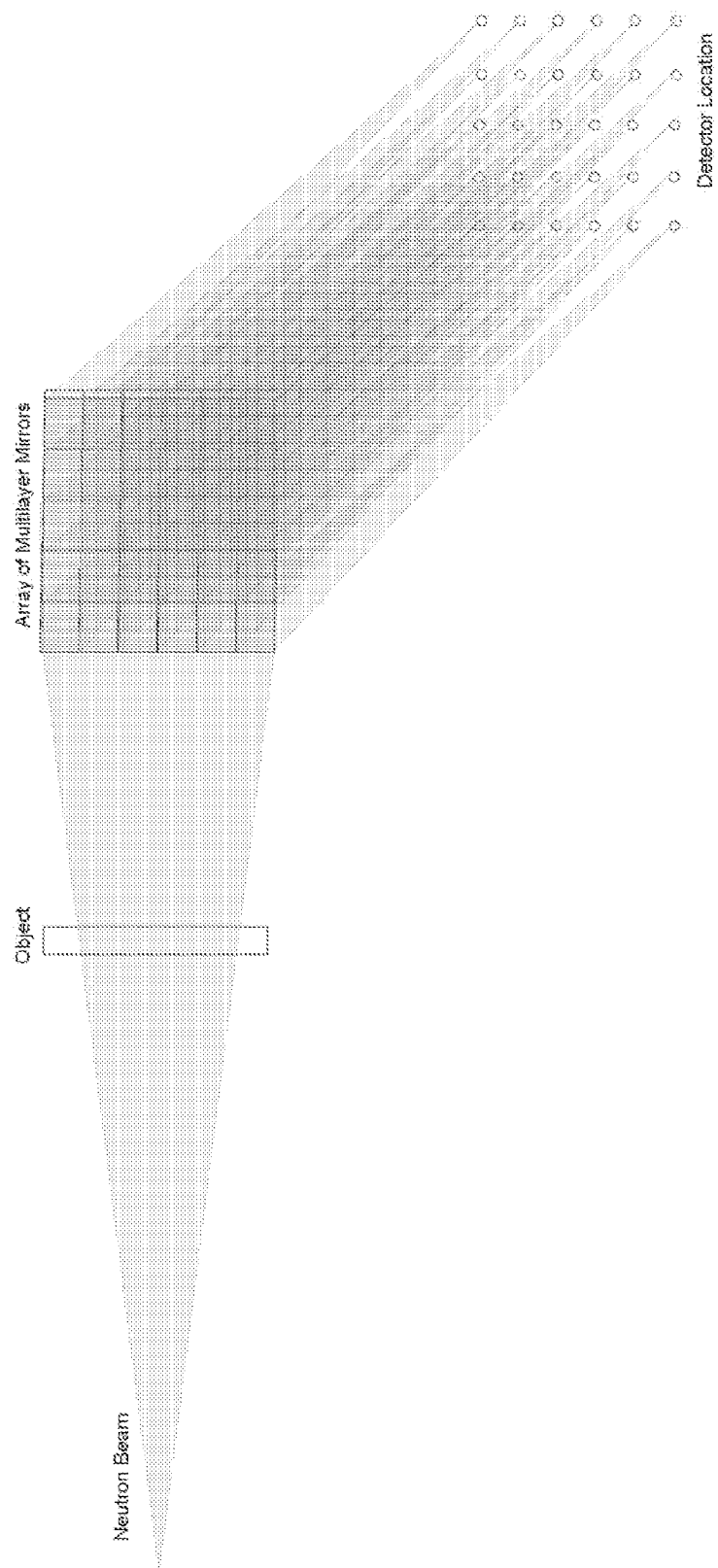
FIG. 7E illustrates a Hartmann sensor with an array of off axis multilayer mirrors.

FIG. 7B illustrates a geometry in which the Hartmann sensor or phase grating are placed in a diverging neutron beam but the determination of the phase and amplitude of the object is performed in a simulated collimated space. This simulated collimated space is similar to the techniques used to more easily analyze curvature wavefront sensors. The object is placed in a diverging neutron beam which is in turn magnified onto the wavefront sensor and onto the 2-D neutron imager. This allows both the phase and the absorption information to be recovered. By placing the object in an expanding beam, there is a large focus term on the phase. There are at least two approaches to recovering the phase in the presence of a large focus term. The first is to use an iterative technique to reconstruct the large phase. A second approach is to perform the phase reconstruction in collimated space. This latter technique is effectively used for curvature wavefront sensor simulations. The far right-hand side shows the geometry of the experiment in which a micro-focus neutron source would reside in the location of the focus of the lens and illuminate the object and neutron mask with a spherically diverging beam which would then be collected with the neutron detector. Each of these devices, the neutron source, the object, the neutron mask and the neutron detector, have an object plane in collimated space on the left-hand side of the lens as shown in FIG. 7B. Thus the simulation can be performed in collimated space with the appropriate magnification placed on each of the objects. FIG. 7C illustrates an example geometry of a Hartmann sensor having an array of neutron zone plates. FIG. 7D illustrates an examplary geometry of a Hartmann sensor having an array of neutron zone plates. FIG. 7E illustrates a Hartmann sensor with an array of off axis multilayer mirrors.

Turning now to FIG. 8A and FIG. 8B, details of a Hartmann mask 800 are shown. FIG. 8A is a frontal ("beam's eye") view of the mask, whereas, FIG. 8B is a cross sectional view of the same. In this embodiment, a transparent substrate 810 is used as the support structure for the absorbing thin-film screen. Based on the example materials listed in Table 1, Si is a good choice for the substrate, given that it is a low-loss material for neutrons. A thin film of a highly absorbing material 820 is grown onto the substrate. A reasonable candidate material for the absorbing mask is Gadolinium, whose relevant parameters are tabulated in Table 1. Other materials with a high neutron absorption cross section include Boron and Cadmium. Based on the material parameters tabulated in Table 1, Gadolinium, for instance, has a 1/e absorption length of 3 μm for thermal neutrons, with a nominal wavelength λ≈4 Angstroms. Thus, the thickness of the thin film 820, h, is in the range of 3 μm to 40 μm, and, more specifically, in the range of 10 μm to 20 μm. The Hartmann screen consists of a regular array of holes 830 with a diameter, w, and a center-to-center distance, or array period, given by v.

The sensitivity expected from a Hartmann sensor can be calculated $$\sigma_{\theta-H} \approx \frac{\pi}{8}\left(\frac{\theta}{SNR}\right) = \frac{\pi}{8}\left(\frac{D}{L}\right)\left(\frac{1}{SNR}\right), \quad (3)$$

where θ is the angular extent (divergence) of the beam 730, D is the source spot size 720, L is the distance between the source and the Hartmann sensor, and, SNR is the signal-to-noise-ratio of the measurement. For a neutron spot size of D=20 microns, a distance between the neutron source and the Hartmann screen of L=20 cm and an SNR of 20, one would expect to measure angular deflections of θ~2 μrad. The Hartmann wave-front sensor is therefore degraded by a larger neutron spot size but it does not have the strict requirement on transverse coherence that the two-dimensional shearing interferometer has.

C.2. A Hartmann Neutron Sensor with Enhanced Performance

The classic Hartmann sensor, including the sensor 700 shown in FIG. 7, characterizes a beam by evaluating the local slope (gradient) of the wavefront across the beam. This is realized by measuring the ensemble of lateral displacement of a grid of spots beyond the Hartmann mask. By placing the detector at distances further removed from the Hartmann mask, the sensitivity improves, since the effective lever arm for the lateral spot displacement increases. In the Hartmann sensor, many of the incident neutrons are absorbed by the Hartmann mask and do not therefore make it to the detector. The sensitivity can be improved in the case of a low fluence neutron source by enabling a larger percentage of the incident neutrons to be incident on the detector. This can be achieved by replacing the Hartmann mask with a Hartmann phase array. The Hartmann phase array can be realized using an array of neutron zone plates, an array of off-axis multilayer mirrors or an array of refractive lenses, however, in the case of refractive lenses in particular there will be significant losses incurred in the lenses themselves.

D. Integration of a Wavefront Sensor with a 2D Solid-State Neutron Detector

In addition to the periodic mask, another key component in the two-dimensional wavefront sensor is a neutron detector. The detector must be capable of sensing a two-dimensional image—the output pattern of the sensor in this case, with reliable performance, high sensitivity, minimal false alarm rates and low noise. One example of such a sensor is a solid-state, compact and rugged two-dimensional neutron detector, based upon a basic detector invented at LLNL. See, for example, U.S. Pat. No. 8,314,400, titled "Method to Planarize Three-Dimensional Structures to Enable Conformal Electrodes," filed Jan. 27, 2011, incorporated herein by reference. See also U.S. patent application Ser. No. 13/456,182; titled "Method for Manufacturing Solid-State Thermal Neutron Detector with Simultaneous High Thermal Neutron Detection Efficiency (>50%) and Large Gamma to Neutron Discrimination (>$10^4$)," filed Apr. 25, 2012, incorporated herein by reference.

The basic prior art detector, which is designed as a non-imaging single-aperture detector can be modified to function in a two-dimensional imaging detection mode. When interfaced with a charge coupled device (ccd) (or equivalent) detector, a compact imaging neutron detector, with a video output capability, can be realized.

Figure 9:
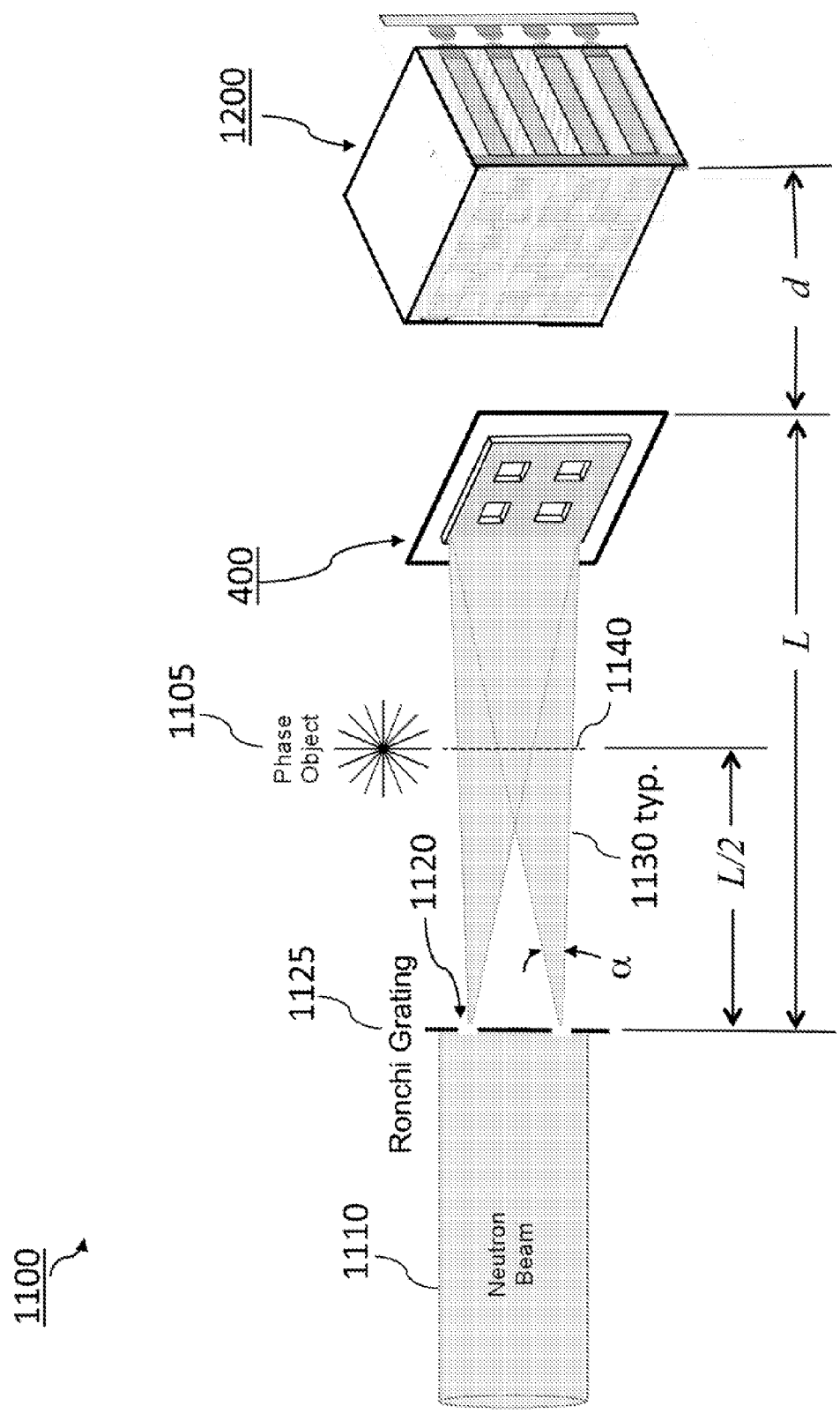
FIG. 9 depicts a two-dimensional neutron interferometer of the invention using a crossed phase grating, a Ronchi extended-source coherency grating and a solid-state 2D pixelated neutron detector.

Turning to FIG. 9, an example of implementing this class of solid-state neutron detector 1200 as a component in a wavefront sensor system 1100 is shown. Without loss of generality, the specific neutron wavefront sensor is shown using a two-dimensional shearing interferometric approach (similar to FIG. 6), with a crossed phase grating 400 as the shearing component and a Ronchi grating 1125 for extended source capability. The remaining elements are described with respect to FIG. 6, and, are not fundamental to the detector or its implementation herein. The input plane of the neutron detector 1200 is positioned at a distance, d, downstream of the grating, with a suitable interface for providing the desired output signal format, etc.

Figure 10:
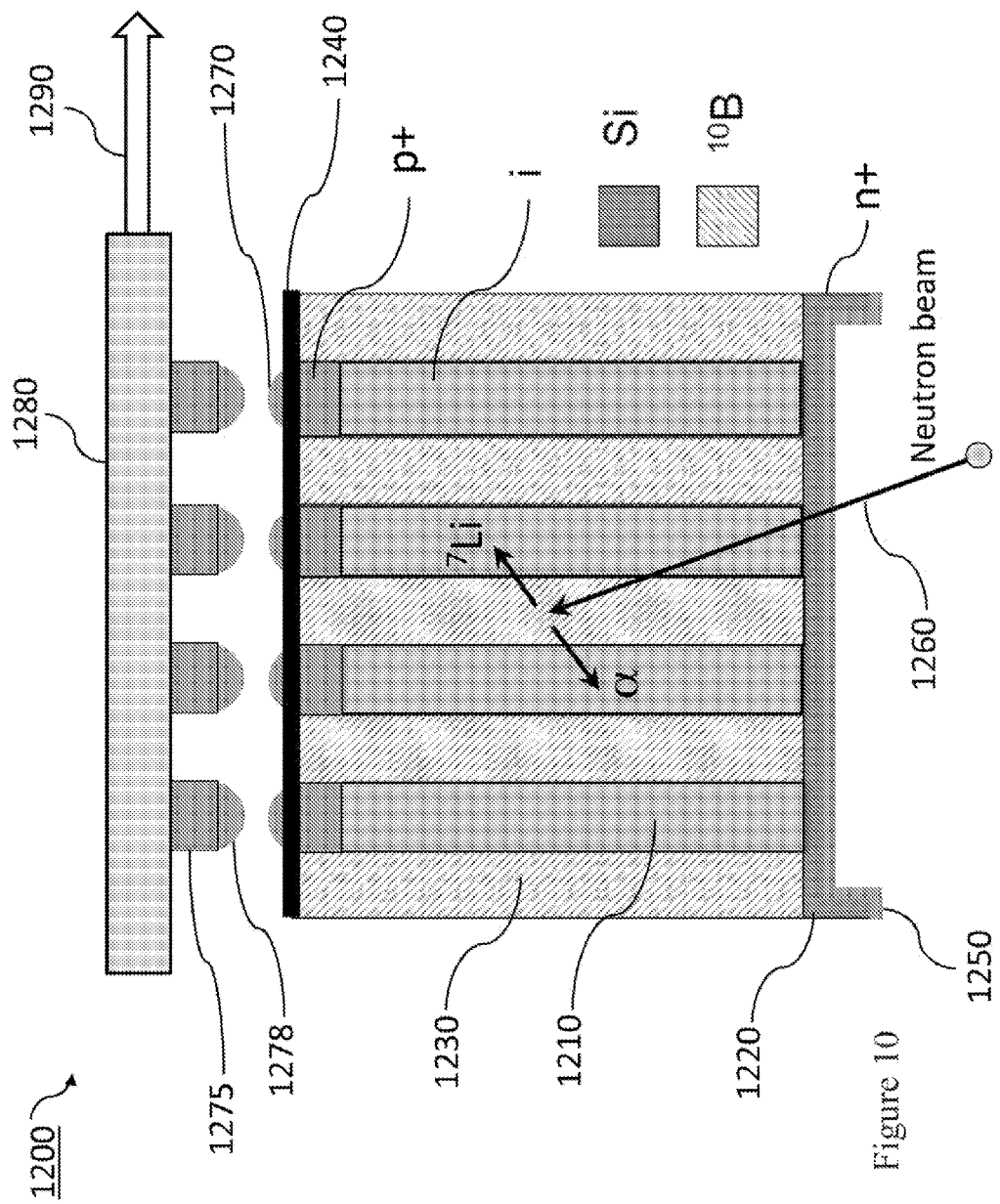
FIG. 10 shows details of the solid-state 2D pixelated neutron detector used in the interferometer of FIG. 11.

The salient features of the neutron detector 1200 are shown in FIG. 10. Detailed, fundamental descriptions and embodiment of the single-aperture detector, its operating principles, material composition and parameters, fabrication and planarization techniques, and basic performance of the detector under a variety of conditions are fully described in the above pair of U.S. patent applications, which are herein incorporated by reference.

As a cursory overview, the basic detector 1200 is comprised of a two-dimensional grid of Si pillars 1210, of high aspect ratio, formed onto a common Si substrate 1220. Intervening layers of a suitable neutron interaction material 1230 such as $^{10}$B, with a high cross section for the production of ionizing product channels, are formed between the Si pillars in the array. The Si pillars are fabricated as a parallel array of p-i-n diodes, with the upper and lower respective surfaces of the pillars electronically connected by suitable conductive surfaces, 1240 and 1250, respectively. During operation, a beam of neutrons is typically incident upon the detector from above (not shown). Upon interaction of a neutron with the $^{10}$B vertical layers, products such as $^7$Li and α-particles are produced. These decay products subsequently interact via ionization in the Si pillars, giving rise to charge carriers, which result in a detectable photocurrent across the entire vertical structure. Since the upper and lower surfaces of the detector are, independently, electrically shorted in the prior art, the entire structure acts as a single, large-area detector, with a parallel array of coupled p-i-n diodes. Hence, the prior art does not reveal spatial information regarding the lateral location of the impinging neutron beam.

Returning to FIG. 10, the basic detector 1200 is modified for application as a two-dimensional neutron detector. First, the basic detector is inverted so that the neutrons 1260 impinge through the lower surface of the detector (the so-called handle, comprised of layers 1220 and 1250), as opposed to the upper surface. This provides electrical access across the upper surface of the detector for multi-pixel functionality. In this imaging embodiment, the planar surface electrode 1240 is not present. Instead, electrical contacts are fabricated onto each individual Si pillar (or, a small cluster of pillars) by an array of corresponding solder bumps 1270, as an example. Using well-known contacting techniques, such as flip-chip technologies, a multi-element, monolithic array of amplifiers and sensors 1280, with underside contacts 1275 and corresponding solder bumps 1278 is contacted to the array of respective Si pillars via its respective solder bump or ball array 1270. Moreover, as opposed to growing a single electrode on the upper surface, individual Si pillars can be addressed via an ensemble of independent electrodes, thereby providing detection of photocurrents independently. Hence, the Si pillars can be individually connected to an appropriate multi-element sensor, such as a charge coupled device (ccd) detector array 1280. Therefore, as neutrons interact in a given region of the detector, the presence of a photocurrent at a given physical Si pillar provides spatial resolution of the event interaction. As shown in the figure, each Si pillar is treated individually. One skilled in the art will appreciate that, depending on the application needs (spatial resolution, S/N, etc.), clusters of Si pillars are be electrically connected, either by employing a large-area common upper electrode or via a programmable coupling of the ccd elements in the sensing module. Also, the upper electrode of the prior art 1240 can be replaced by a thin film of a highly absorbing neutron layer, yet, electrically insulating material, such as Gd, whose 1/e absorption length is ≈3 μm for thermal neutrons. An array of small apertures can be formed across the surface of the Gd layer to allow the solder bump array 1270 to protrude in order to enable electrical contacting to the ccd respective solder-bump array 1278. The presence of this layer can provide additional shielding of neutrons from adversely affecting the ccd detector/amplifier array. The video output 1290 of the ccd array therefore provides spatial information regarding the physical pillar (or, pixel) where the neutron impinged. Various post-processing techniques (which can be programmable and, further, be on-chip) can be implemented, including multi-pixel centroid algorithms, temporal integration and gating, analog or digital processing, etc. for enhanced imaging capabilities. Output 1290 may be input into a processor 1295 for analysis.

E. Simulated Performance of the 2-D Neutron Shearing Interferometer and Hartmann Screen E.1. System Architecture and Simulation Parameters A comparison of the two-dimensional shearing interferometer and Hartmann sensor is presented herein. In both simulations, cold neutrons were assumed with a neutron beam diverging with an f-number of 3000, where the f-number is defined as the focal length of the focusing optic divided by the diameter of the neutron beam. The wavefront of the neutron source is assumed to be reproducible in all the simulations. In the case of the shearing interferometer, the simulation assumes the system shown in FIG. 3 and, employing the crossed phase grating shown in FIGS. 4A through 4E. Referring to these Figures for dimensional labels, the phase grating is situated three meters from the source (L=3 m), the detector is located 15 mm past the plane containing the orthogonal phase gratings (d=15 mm), and the phase object is situated at the mid-plane between the neutron focus and the crossed phase grating (L/2=1.5 m). The crossed grating was simulated with bar and slit widths both equal to 12.5 μm (q=p/2=12.5 μm), thus producing 80 spots across the detector. Given the three-meter separation of the grating plane from the focal plane of the neutron source, the spot size of the neutron beam at the grating plane has a diameter of 1 mm.

The simulation involves determining the phase of the object based on the field measurement by the shearing interferometer. In both of these simulations, there is a significant focus term to the phase, which must be accurately recovered in order to recover the phase of an object placed in the beam or the residual aberrations in the beam itself. These simulations utilize an iterative reconstruction technique to accurately recover the small phase perturbations within the large focus term, discussed next.

E.2. Iterative Wavefront Reconstruction Approach and Algorithm

The iterative reconstruction process for the neutron wavefront is very similar to that of a closed-loop adaptive optics system. In a typical closed-loop adaptive optics application, an initial electric field, defined by a phase and amplitude, enters an optical system and is relay imaged onto a deformable mirror and subsequently onto a wave-front sensor. In the case of a two-dimensional shearing interferometer wavefront sensor, a two-dimensional grating is used to form a spot pattern on the wave-front sensor camera. The difference between the locations of these spots and a set of reference spots (the latter generated assuming that a nearly perfect wavefront enters the system) is used to determine the local gradients in the wavefront. The wavefront is then reconstructed from these local gradients. Through the use of a gain factor, a percentage of the calculated wavefront is used to change the shape of the deformable mirror. This procedure proceeds through a sequence of iterations. Convergence is achieved when the measured spots from subsequent iterations approach the reference spot locations. At this point, equiphase surface of the beam approaches that of a nearly perfect wavefront.

Figure 11:
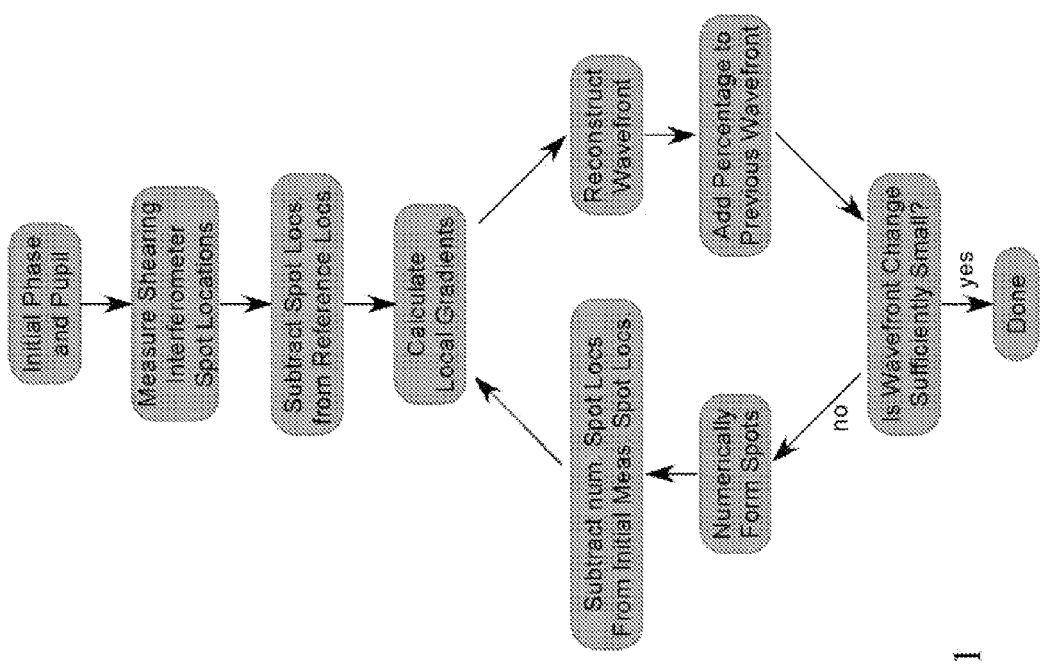
FIG. 11 shows a computational flowchart for an open-loop iterative phase reconstruction algorithm used in system simulations.

A flow chart of the algorithm used in the simulations below is shown in FIG. 11. The primary difference between the closed-loop application described above and the iterative reconstruction process is that rather than driving the solution to reference centroid locations with the use of a deformable mirror, the phase is driven to the initial measured centroid locations using a simulation loop. This is accomplished numerically by using the reconstructed phase to form simulated shearing interferometer spots on a simulated wave-front sensor camera and then comparing the numerically formed spots to the initial measured spots. The gradients are then calculated from the differences between the simulated spot locations and the measured spot locations. Although the initial measured spots contain detector noise, no noise is added to the simulated shearing interferometer spots. The wavefront is reconstructed from these gradients, and a numeric gain factor is used to add a percentage of the reconstructed wavefront to the composite wavefront from the previous iterations. In this approach the simulated shearing interferometer spot locations are driven towards the measured spot locations. Hence, the reconstructed wavefront is driven to that of the initial measured wavefront. Using this technique, errors in the boundary conditions can be significantly reduced and large aberrations can be reconstructed with very low phase variance between the initial phase and the reconstructed phase.

Both simulations discussed below utilize equivalent wave-optics simulations to propagate the electric field between the various planes. The grating structure and the phase object are added to the electric field after the field has been propagated to their respective locations. The wavefront is reconstructed from the simulated spots by first locating the displacement of each of the spots with a center-of-mass centroider and, subsequently, reconstructing the resulting gradients with a multi-grid wavefront reconstructor, as is known in the art of adaptive optical reconstruction algorithms.

The simulations involve using a neutron source to determine the phase of an unknown object placed in the beam. This application is simulated with an expanding beam, which is typical for most systems. The reconstruction process for an expanding beam is much more computationally intensive than that for a collimated beam owing to the large focus term, which dominates the phase measurement.

E.3. Reconstruction of a Phase Object Using a 2D Shearing Interferometer

Figure 12A:
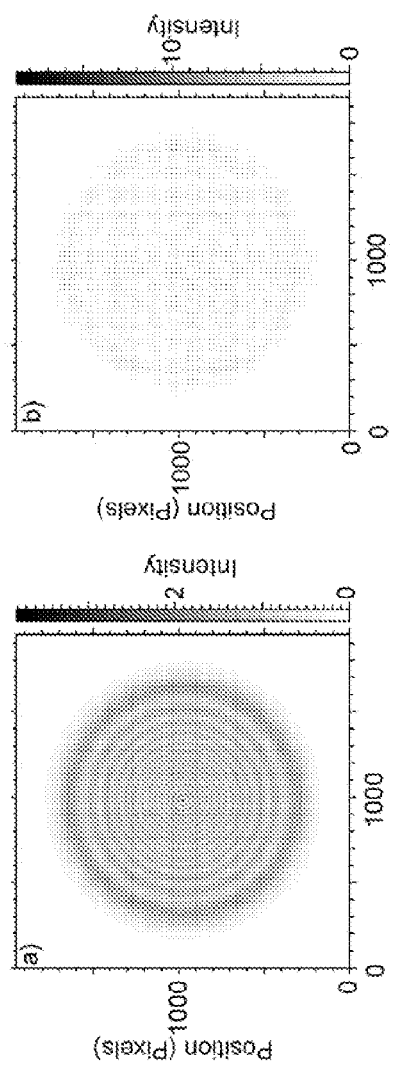
FIG. 12A shows a simulated intensity profile at the entrance of a crossed phase grating of the shearing interferometer, without a phase object in the beam path.
Figure 12B:
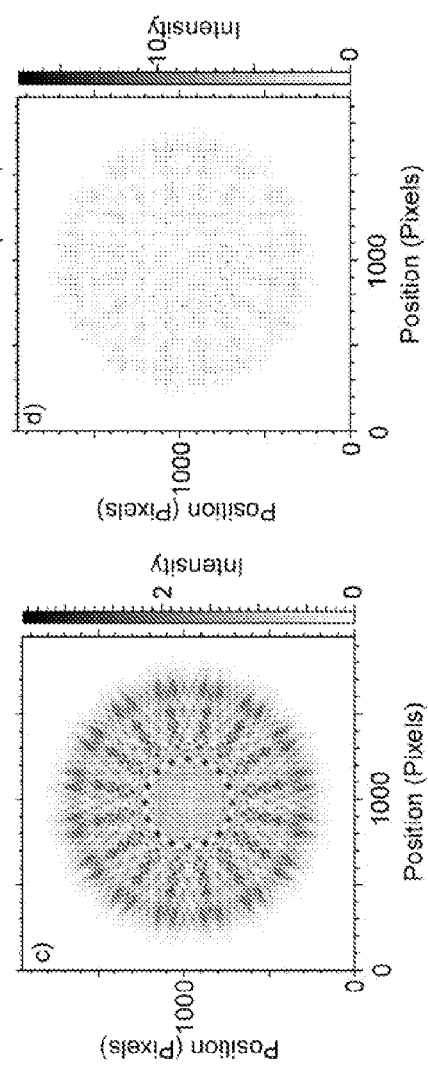
FIG. 12B shows a simulated intensity profile at 15 mm downstream of, and, after passage through, the crossed phase grating of the shearing interferometer, without a phase object in the beam path.
Figure 12C:
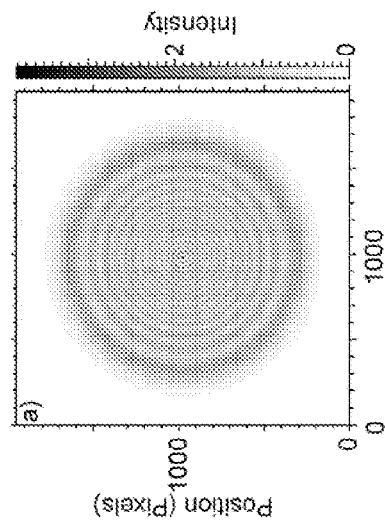
FIG. 12C shows a simulated intensity profile at the entrance of a crossed phase grating of the shearing interferometer, with a test phase object in the beam path.
Figures 15A, 15B, 15C:
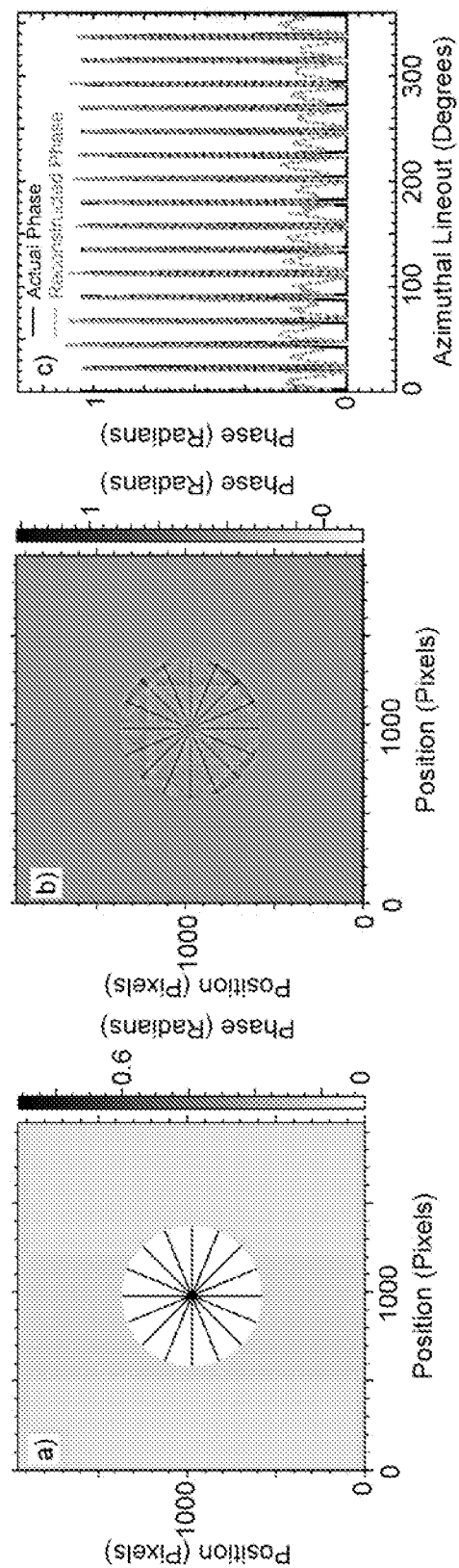
FIG. 15A shows the phase map of the "actual" star-shaped phase object used in the crossed-phase-grating simulations.
FIG. 15B shows results of the reconstructed test phase object.
FIG. 15C shows an azimuthal lineout through the actual phase object, of FIG. 15A and the reconstructed phase object of FIG. 15B, both taken at one-fourth of the respective object's diameter.

In the case of the two-dimensional shearing interferometer, a star-shaped phase object is placed midway between the aperture placed in front of the neutron beam and the crossed phase gratings. FIGS. 12A and 12B represent, respectively, the intensity patterns at the plane of the crossed phase gratings and 15 mm past the plane (the detector location), respectively, with no phase object in the beam. (FIG. 3 shows the positions of the grating plane and the detector plane, which are located at a distance, L, and at a distance L+d, from the pinhole 320, respectively.) FIGS. 14C and 14D represent, respectively, the intensity patterns at the plane of the crossed phase gratings and 15 mm past the plane, respectively, with the star-shaped phase object in the beam. FIG. 15A shows the phase map of the "actual" star-shaped phase object used in the crossed-phase-grating simulations.

Figure 12D:
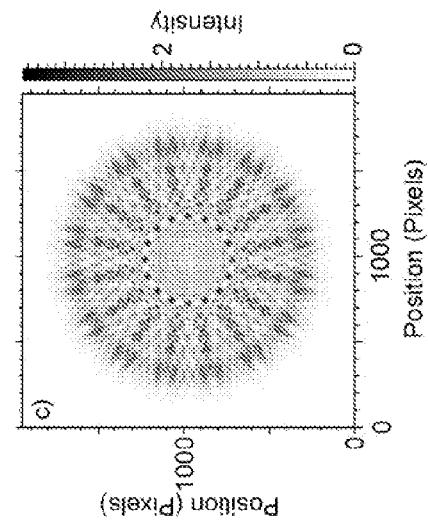
FIG. 12D shows a simulated intensity profile at 15 mm downstream of, and, after passage through, the crossed phase grating of the shearing interferometer, with a test phase object in the beam path.

Given the "measured" spot patterns, as simulated in FIGS. 12B and 12D, the local gradients are determined, the phase reconstructed, and the amplitude solved for the neutron field at the entrance to the crossed phase gratings. The resultant fields are then back-propagated to the location where the phase object was placed in the beam. The two phases are then subtracted and the resultant phase unwrapped using a multi-grid algorithm to determine the phase of the object.

Figures 13A, 13B, 13C:
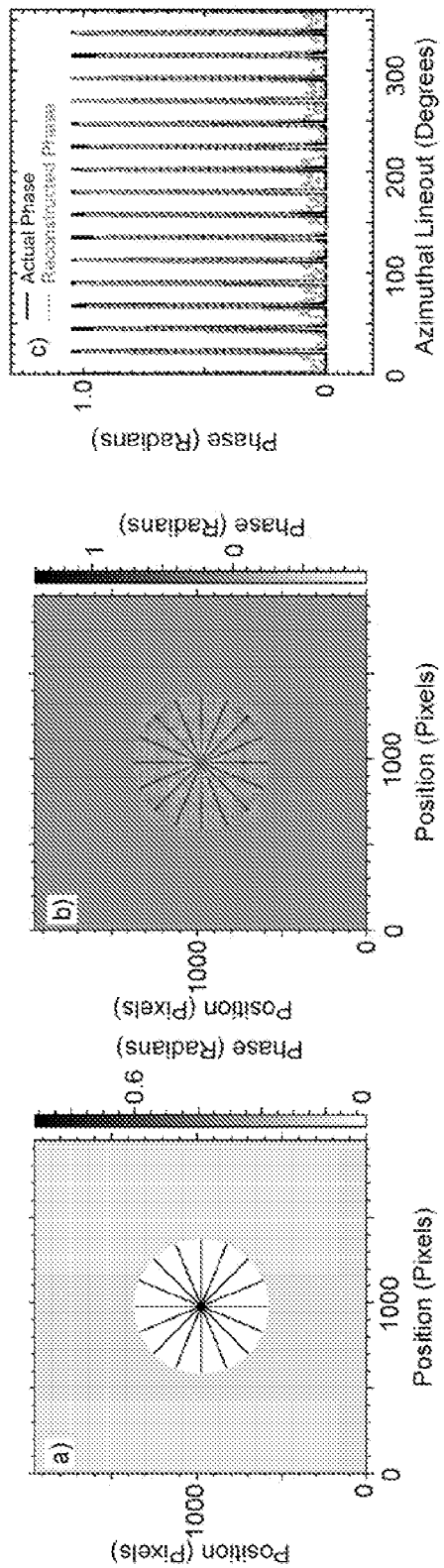
FIG. 13A shows a phase map of the "actual" test object used in the simulations for FIGS. 14C and 14D.
FIG. 13B shows results of the reconstructed test phase object, shown in FIG. 15A.
FIG. 13C shows an azimuthal lineout through the actual phase object of FIG. 15A and the reconstructed phase object of FIG. 15B, both taken at one-fourth of the respective object's diameter.

The results of this phase recovery process are shown in FIGS. 13B and 13C. FIG. 13B shows results of the reconstructed phase map of the phase object (the actual phase object map is shown in FIG. 13A). FIG. 13C shows an azimuthal lineout at a radius of one fourth the object's diameter for both the actual (black line), and reconstructed phases (dashed gray line), as shown in FIGS. 13A and 13B, respectively. This lineout illustrates that the amplitude and spatial frequency of the phase object are quantitatively reproduced. There is a slight high-spatial-frequency degradation as evidenced by the slope of the edges in the reconstructed phase vs. the actual phase and a low-frequency noise term present in the reconstructed phase. The mean error in the full-width-at-half-maximum and the amplitude between the reconstructed vs. applied phase bars, for the two-dimensional shearing interferometer, as shown in FIG. 15C, was computed to be 14.7% and 3.49%, respectively.

E.4. Reconstruction of a Phase Object Using a 2D Hartmann Screen

In the case of the two-dimensional Hartmann screen, a star-shaped phase object is placed midway between the aperture placed in front of the neutron beam and the Hartmann screen, as was the case with the shearing interferometer simulations above. FIGS. 14A and 14B represent, respectively, the intensity patterns at the plane of the Hartmann screen and 15 mm past the plane (the detector location), respectively, with no phase object in the beam. (FIG. 7 shows the positions of the Hartmann screen and the detector plane, which are located at a distance, L, and at a distance L+d, from the pinhole 720, respectively.) FIGS. 14C and 14D represent, respectively, the intensity patterns at the plane of the Hartmann screen and 15 mm past the plane, respectively, with the star-shaped phase object in the beam. FIG. 15A shows the phase map of the "actual" star-shaped phase object used in the Hartmann-screen simulations.

Given the "measured" spot patterns, as simulated in FIGS. 14B and 14D, the local gradients are determined, the phase reconstructed, and the amplitude solved for the neutron field at the entrance to the Hartmann screen. The resultant fields are then back-propagated to the location where the phase object was placed in the beam. The two phases are then subtracted and the resultant phase unwrapped using a multi-grid algorithm to determine the phase of the object.

The results of this phase recovery process, in the case of the Hartmann screen, are shown in FIGS. 15B and 15C. FIG. 15B shows results of the reconstructed phase map of the phase object (recall, the actual phase object map is shown in FIG. 15A). FIG. 15C shows an azimuthal lineout at a radius of one fourth the object's diameter for both the actual (black line), and reconstructed phases (dashed gray line), as shown in FIGS. 15A and 15B, respectively. This lineout illustrates that the amplitude and spatial frequency of the phase object are quantitatively reproduced. Again, there is a slight high-spatial-frequency degradation as evidenced by the slope of the edges in the reconstructed phase vs. the actual phase and a low-frequency noise term present in the reconstructed phase. The mean error in the full-width-at-half-maximum and the amplitude between the reconstructed vs. applied phase bars, for the two-dimensional Hartmann screen, as shown in FIG. 15C, was computed to be 9.43% and 1.94%, respectively.

The embodiments disclosed were meant only to explain the principles of the invention and its practical application to thereby enable others skilled in the art to best use the invention in various embodiments and with various modifications suited to the particular use contemplated. The scope of the invention is to be defined by the following claims.

I claim:

1. Apparatus for two-dimensional neutron imaging of a sample comprising:
    a beam coherence generator on which a neutron beam is incident and which transmits a substantially coherent neutron beam therethrough;
    a two-dimensional structure with periodic features in a pair of transverse orthogonal dimensions spaced from the beam coherence generator, wherein a sample can be positioned between the beam coherence generator and the structure so that the coherent beam from the beam coherence generator passes through the sample and the resulting encoded beam is incident on the structure, wherein the two-dimensional structure is a two-dimensional Hartmann amplitude mask or phase screen as embodied by a two-dimensional array of zone plates, multilayer off-axis mirrors or refractive lenses; and
    a neutron detector positioned after the two-dimensional structure to detect both phase shift and absorption of neutrons passing through the sample.

2. The apparatus of claim 1, further comprising a neutron source for producing the beam incident on the beam coherence generator wherein the neutron source is a noncoherent source.

3. The apparatus of claim 1, wherein the beam coherence generator is a pinhole.

4. The apparatus of claim 1, wherein the beam coherence generator is a two-dimensional Ronchi grating.

5. The apparatus of claim 1, wherein the detector is a two-dimensional detector array.

6. The apparatus of claim 5, wherein the detector comprises a two-dimensional pixilated solid state neutron detector.

7. The apparatus of claim 6, wherein the detector comprises:
    a substrate;
    a two-dimensional grid of high aspect pillars formed on the substrate and forming a parallel array of p-i-n diodes;
    intervening layers of neutron interaction material formed between the pillars, the material having a high cross-section for producing ionizing products in response to incident neutrons;
    a planar surface electrode formed on the substrate on the opposed side from the pillars;
    an electrical contact formed on the distal end from the substrate of each pillar or on small clusters of pillars; and
    an amplifier and sensor array having corresponding electrical contacts that contact each contact on the pillars.

8. The apparatus of claim 7, wherein the substrate and pillars are formed of Si and the neutron interaction material is $^{10}B$.

9. The apparatus of claim 7, wherein the electrical contacts on the pillars and amplifier and sensor array are solder bumps.

10. The apparatus of claim 7, further comprising a processor connected to the output of the amplifier and sensor array.

11. The apparatus of claim 1, wherein the sample is positioned at a plane between the beam coherence generator and the two-dimensional structure.

12. The apparatus of claim 1, wherein the apparatus is configured as a Talbot imaging system.

13. The apparatus of claim 1, wherein the Hartmann mask or screen comprises an amplitude mask formed of a substantially highly neutron absorbing material laving a two-dimensional array of highly neutron transmitting apertures formed therein.

14. The apparatus of claim 13, wherein the amplitude mask comprises a substantially neutron transparent substrate and a substantially neutron absorbing layer formed on the substrate, the neutron absorbing layer having a two-dimensional periodic array of spaced apertures formed therein.

15. The apparatus of claim 14, wherein the neutron absorbing layer is formed of gadolinium, boron, or cadmium.

16. Apparatus for two-dimensional neutron imaging of a sample comprising:
- a beam coherence generator on which a neutron beam is incident and which transmits a substantially coherent neutron beam therethrough;
- a two-dimensional structure with periodic features in a pair of transverse orthogonal dimensions spaced from the beam coherence generator, wherein a sample can be positioned between the beam coherence generator and the structure so that the coherent beam from the beam coherence generator passes through the sample and the resulting encoded beam is incident on the structure; and
- a neutron detector positioned after the two-dimensional structure to detect both phase shift and absorption of neutrons passing through the sample wherein the detector is a two-dimensional detector array, wherein the detector comprises a two-dimensional pixilated solid state neutron detector, wherein the detector comprises:
- a substrate;
- a two-dimensional grid of high aspect pillars formed on the substrate and forming a parallel array of p-i-n diodes;
- intervening layers of neutron interaction material formed between the pillars, the material having a high cross-section for producing ionizing products in response to incident neutrons;
- a planar surface electrode formed on the substrate on the opposed side from the pillars;
- an electrical contact formed on the distal end from the substrate of each pillar or on small clusters of pillars; and
- an amplifier and sensor array having corresponding electrical contacts that contact each contact on the pillars, and wherein the sensors of the amplifier and sensor array are charge coupled devices.

* * * * *